(12) United States Patent
Han et al.

(10) Patent No.: US 8,999,343 B2
(45) Date of Patent: Apr. 7, 2015

(54) ANTIBODIES THAT BIND MYOSTATIN, COMPOSITIONS AND METHODS

(75) Inventors: Huiquan Han, Thousand Oaks, CA (US); Taruna Arora, Thousand Oaks, CA (US); Qing Chen, Oxnard, CA (US); Hsieng Sen Lu, Westlake Village, CA (US); Xiaolan Zhou, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/816,894

(22) PCT Filed: Aug. 15, 2011

(86) PCT No.: PCT/US2011/047806
§ 371 (c)(1),
(2), (4) Date: Apr. 29, 2013

(87) PCT Pub. No.: WO2012/024242
PCT Pub. Date: Feb. 23, 2012

(65) Prior Publication Data
US 2013/0209489 A1    Aug. 15, 2013

Related U.S. Application Data

(60) Provisional application No. 61/374,095, filed on Aug. 16, 2010.

(51) Int. Cl.
C07K 16/26    (2006.01)
C07K 16/22    (2006.01)
A61K 39/00    (2006.01)

(52) U.S. Cl.
CPC .............. C07K 16/26 (2013.01); C07K 16/22 (2013.01); *A61K 2039/505* (2013.01); *C07K 2317/34* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,368,597 B1 | 4/2002 | Strassmann et al. |
| 7,261,893 B2 | 8/2007 | Veldman et al. |
| 7,320,789 B2 | 1/2008 | Dunham et al. |
| 7,371,726 B2 | 5/2008 | Junker et al. |
| 7,511,012 B2 | 3/2009 | Han et al. |
| 7,534,432 B2 | 5/2009 | Lee et al. |
| 7,585,648 B2 | 9/2009 | Junker et al. |
| 7,632,499 B2 | 12/2009 | Davies et al. |
| 7,635,760 B2 | 12/2009 | Han et al. |
| 7,655,763 B2 | 2/2010 | Veldman et al. |
| 7,731,961 B1 | 6/2010 | Aghajanian et al. |
| 7,785,587 B2 | 8/2010 | Whittemore et al. |
| 7,803,923 B2 | 9/2010 | Han et al. |
| 7,807,159 B2 | 10/2010 | Chin et al. |
| 7,892,561 B2 | 2/2011 | Junker et al. |
| 7,928,075 B2 | 4/2011 | Han et al. |
| 7,947,646 B2 | 5/2011 | Sun et al. |
| 8,063,188 B2 | 11/2011 | Sayers et al. |
| 8,066,995 B2 | 11/2011 | Davies et al. |
| 8,067,562 B2 | 11/2011 | Han et al. |
| 8,071,538 B2 | 12/2011 | Han et al. |
| 8,092,798 B2 | 1/2012 | Aghajanian et al. |
| 8,309,082 B2 | 11/2012 | Han et al. |
| 8,410,043 B2 | 4/2013 | Sun et al. |
| 8,501,678 B2 | 8/2013 | Sun et al. |
| 2007/0149458 A1 | 6/2007 | Han et al. |
| 2011/0008375 A1 | 1/2011 | Hq et al. |
| 2011/0091455 A1 | 4/2011 | Chin et al. |
| 2011/0183897 A1 | 7/2011 | Sun et al. |
| 2011/0281796 A1 | 11/2011 | Han et al. |
| 2011/0293630 A1 | 12/2011 | Stitt et al. |
| 2012/0083442 A1 | 4/2012 | Han et al. |
| 2012/0107928 A1 | 5/2012 | Aghajanian et al. |
| 2013/0030159 A1 | 1/2013 | Han et al. |
| 2013/0122007 A1 | 5/2013 | Stitt et al. |

FOREIGN PATENT DOCUMENTS

| | | |
|---|---|---|
| CN | 1788019 A | 6/2006 |
| CN | 101272802 A | 9/2008 |
| WO | WO 2004/037861 A2 | 5/2004 |
| WO | WO 2004/058988 | 7/2004 |
| WO | WO 2004/101511 A2 | 11/2004 |
| WO | WO 2006/116269 A2 | 11/2006 |
| WO | WO 2006116269 A2 * | 11/2006 |
| WO | WO 2007/053775 A1 | 5/2007 |
| WO | WO 2007/067616 A2 | 6/2007 |
| WO | WO 2008/031061 A2 | 3/2008 |
| WO | WO 2008/109167 A2 | 9/2008 |
| WO | WO 2010/062383 A2 | 6/2010 |
| WO | WO 2012/024242 | 2/2012 |
| WO | WO 2013/106175 A1 | 7/2013 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
PCT International Search Report and Written Opinion, PCT/US3022/047806, Dec. 6, 2011, 13 Pages.
Wagner, K., et al., "A Phase I/II trial of MYO-029 in Adult Subjects with Muscular Dystrophy," Annals of Neurology, May 2008, pp. 561-571, vol. 63, No. 5.
First Examination Report for New Zealand Patent Application No. 608206, Jul. 12, 2013, 3 Pages.
Krivickas, L., et al., "Single Muscle Fiber Contractile Properties in Adults With Muscular Dystrophy Treated With MYO-029," Muscle & Nerve, Jan. 2009, pp. 3-9.

(Continued)

*Primary Examiner* — Brian J Gangle
*Assistant Examiner* — Andrea McCollum
(74) *Attorney, Agent, or Firm* — Fenwick & West LLP

(57) ABSTRACT

Myostatin antagonists, including myostatin binding antibodies, are disclosed. Also disclosed are nucleic acids encoding and cells including myostatin antagonists; methods of production; and methods of use.

10 Claims, 8 Drawing Sheets

(56) References Cited

OTHER PUBLICATIONS

Office Action for Australian Patent Application No. 2011292197, Jan. 23, 2014, 3 Pages.

First Office Action for Chinese Patent Application No. CN 201180044739.7, Mar. 13, 2014, 12 Pages.

Eurasian Office Action, Eurasian Application No. 201390242/28, Oct. 31, 2014, 5 pages.

Chinese Second Office Action, Chinese Application No. 201180044739.7, Jan. 9, 2015, 8 pages.

* cited by examiner

SEQUENCE LISTING

<160> NUMBER OF SEQ ID NOS: 55

<210> SEQ ID NO 1
<211> LENGTH: 107
<212> TYPE: PRT
<213> ORGANISM: Artificial Sequence
<220> FEATURE:
<223> OTHER INFORMATION: Description of Artificial Sequence: Synthetic
      12A5-1LC polypeptide

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Ser Thr Leu Gln Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys
            100                 105

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      12A5-3LC polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Ser Phe Leu Gln Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys
            100                 105

<210> SEQ ID NO 3
<211> LENGTH: 107
<212> TYPE: PRT
<213> ORGANISM: Artificial Sequence
<220> FEATURE:
<223> OTHER INFORMATION: Description of Artificial Sequence: Synthetic
      12A5-5LC polypeptide

<400> SEQUENCE: 3

Asp Ile Gln Met Thr Gln Ser Pro Ser Ser Leu Ser Ala Ser Val Gly
1               5                   10                  15

```
Asp Arg Val Thr Ile Thr Cys Lys Ala Ser Gln Asp Ile Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Ser Trp Leu Gln Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys
            100                 105

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      12A5-6LC polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Ser Phe Leu Gln Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Ala Leu Leu Tyr
                85                  90                  95

Thr Phe Gly Gln Gly Thr Lys Leu Glu Ile Lys
            100                 105

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      12A5-8LC polypeptide

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Val Ala Trp Tyr Gln Gln Lys Pro Gly Lys Ala Pro Lys Leu Leu Ile
        35                  40                  45

Tyr Tyr Lys Thr Leu Gln Pro Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Asn Leu Leu Tyr
                85                  90                  95
```

```
Thr Phe Gly Gln Gly Thr Lys Leu Glu Ile Lys
            100                 105

<210> SEQ ID NO 6
<211> LENGTH: 107
<212> TYPE: PRT
<213> ORGANISM: Artificial Sequence
<220> FEATURE:
<223> OTHER INFORMATION: Description of Artificial Sequence: Synthetic
      12A5-9LC polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Arg Thr Leu Gln Pro Gly Val Pro Ser Arg Phe Ser Gly
 50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys
            100                 105

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      12A5-10LC polypeptide

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Ser Thr Leu Gln Pro Gly Val Pro Ser Arg Phe Ser Gly
 50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Asn Lys Leu Tyr
                85                  90                  95

Thr Phe Gly Gln Gly Thr Lys Leu Glu Ile Lys
            100                 105

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      12A5-12LC polypeptide

<400> SEQUENCE: 8
```

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Ser Trp Leu Gln Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys
            100                 105
```

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      12A5-18LC polypeptide

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Ser His Leu Gln Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys
            100                 105
```

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      consensus LC polypeptide
<220> FEATURE:
<221> NAME/KEY: MOD_RES
<222> LOCATION: (52)..(52)
<223> OTHER INFORMATION: Lys, Arg or Ser
<220> FEATURE:
<221> NAME/KEY: MOD_RES
<222> LOCATION: (53)..(53)
<223> OTHER INFORMATION: Thr, Phe, Trp or His
<220> FEATURE:
<221> NAME/KEY: MOD_RES
<222> LOCATION: (93)..(93)
<223> OTHER INFORMATION: Asn or Ala
<220> FEATURE:
<221> NAME/KEY: MOD_RES
<222> LOCATION: (94)..(94)
<223> OTHER INFORMATION: Leu or Lys

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Val Ala Trp Tyr Gln Gln Lys Pro Gly Lys Ala Pro Lys Leu Leu Ile
        35                  40                  45

Tyr Tyr Thr Xaa Xaa Leu Gln Pro Gly Val Pro Ser Arg Phe Ser Gly
    50                  55                  60

Ser Gly Ser Gly Thr Asp Phe Thr Phe Thr Ile Ser Ser Leu Gln Pro
65              70                  75                  80

Glu Asp Ile Ala Thr Tyr Tyr Cys Leu Gln Tyr Asp Xaa Xaa Leu Tyr
                85                  90                  95

Thr Phe Gly Gln Gly Thr Lys Leu Glu Ile Lys
            100                 105
```

<210> SEQ ID NO 11
<211> LENGTH: 115
<212> TYPE: PRT
<213> ORGANISM: Artificial Sequence
<220> FEATURE:
<223> OTHER INFORMATION: Description of Artificial Sequence: Synthetic
      12A5-1HC polypeptide

<400> SEQUENCE: 11

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asn Ala Lys Asn Ser
65              70                  75                  80

Leu Tyr Leu Gln Met Asn Ser Leu Arg Ala Glu Asp Thr Ala Val Tyr
                85                  90                  95

Tyr Cys Ala Arg Gly Leu Asp Tyr Trp Gly Gln Gly Thr Thr Val Thr
            100                 105                 110

Val Ser Ser
        115
```

<210> SEQ ID NO 12
<211> LENGTH: 115
<212> TYPE: PRT
<213> ORGANISM: Artificial Sequence
<220> FEATURE:
<223> OTHER INFORMATION: Description of Artificial Sequence: Synthetic
      12A5-3HC polypeptide

<400> SEQUENCE: 12

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Trp Cys Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Glu
    50                  55                  60
```

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Thr Glu Gly Leu Asp Tyr Trp Gly Gln Gly Thr Thr Val Thr
            100                 105                 110

Val Ser Ser
        115

<210> SEQ ID NO 13
<211> LENGTH: 115
<212> TYPE: PRT
<213> ORGANISM: Artificial Sequence
<220> FEATURE:
<223> OTHER INFORMATION: Description of Artificial Sequence: Synthetic
      12A5-5HC polypeptide
<220> FEATURE:
<221> NAME/KEY: MOD_RES
<222> LOCATION: (50)..(50)
<223> OTHER INFORMATION: Any naturally occurring amino acid

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Asn Trp Val Arg Gln Ala Pro Gly Lys Gly Leu Glu Trp Val
        35                  40                  45

Ala Xaa Ile Arg Leu Lys Ser Asp Asn Tyr Ala Thr His Tyr Ala Glu
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Thr Glu Gly Leu Asp Tyr Trp Gly Gln Gly Thr Thr Val Thr
            100                 105                 110

Val Ser Ser
        115

<210> SEQ ID NO 14
<211> LENGTH: 115
<212> TYPE: PRT
<213> ORGANISM: Artificial Sequence
<220> FEATURE:
<223> OTHER INFORMATION: Description of Artificial Sequence: Synthetic
      12A5-6HC polypeptide

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Leu Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr 85                  90                  95

Tyr Cys Thr Glu Gly Leu Asp Tyr Trp Gly Gln Gly Thr Thr Val Thr
                100                 105                 110

Val Ser Ser
        115

<210> SEQ ID NO 15
<211> LENGTH: 115
<212> TYPE: PRT
<213> ORGANISM: Artificial Sequence
<220> FEATURE:
<223> OTHER INFORMATION: Description of Artificial Sequence: Synthetic
      12A5-8HC polypeptide

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Trp Cys Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Thr Glu Gly Leu Asp Tyr Trp Gly Gln Gly Thr Thr Val Thr
                100                 105                 110

Val Ser Ser
        115

<210> SEQ ID NO 16
<211> LENGTH: 115
<212> TYPE: PRT
<213> ORGANISM: Artificial Sequence
<220> FEATURE:
<223> OTHER INFORMATION: Description of Artificial Sequence: Synthetic
      12A5-9HC polypeptide

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Trp Cys Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Thr Glu Gly Leu Asp Tyr Trp Gly Gln Gly Thr Thr Val Thr
                100                 105                 110

Val Ser Ser
        115

```
<210> SEQ ID NO 17
<211> LENGTH: 115
<212> TYPE: PRT
<213> ORGANISM: Artificial Sequence
<220> FEATURE:
<223> OTHER INFORMATION: Description of Artificial Sequence: Synthetic
      12A5-10HC polypeptide

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Trp Cys Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Thr Glu Gly Leu Asp Tyr Trp Gly Gln Gly Thr Thr Val Thr
            100                 105                 110

Val Ser Ser
        115

<210> SEQ ID NO 18
<211> LENGTH: 115
<212> TYPE: PRT
<213> ORGANISM: Artificial Sequence
<220> FEATURE:
<223> OTHER INFORMATION: Description of Artificial Sequence: Synthetic
      A12A5-12HC polypeptide

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Leu Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Thr Glu Gly Leu Asp Tyr Trp Gly Gln Gly Thr Thr Val Thr
            100                 105                 110

Val Ser Ser
        115

<210> SEQ ID NO 19
<211> LENGTH: 115
<212> TYPE: PRT
<213> ORGANISM: Artificial Sequence
<220> FEATURE:
<223> OTHER INFORMATION: Description of Artificial Sequence: Synthetic
      12A5-18HC polypeptide

<400> SEQUENCE: 19
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Trp Cys Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Thr Glu Gly Leu Asp Tyr Trp Gly Gln Gly Thr Thr Val Thr
            100                 105                 110

Val Ser Ser
        115

<210> SEQ ID NO 20
<211> LENGTH: 115
<212> TYPE: PRT
<213> ORGANISM: Artificial Sequence
<220> FEATURE:
<223> OTHER INFORMATION: Description of Artificial Sequence: Synthetic
      consensus HC polypeptide
<220> FEATURE:
<221> NAME/KEY: MOD_RES
<222> LOCATION: (30)..(30)
<223> OTHER INFORMATION: Ser or Arg
<220> FEATURE:
<221> NAME/KEY: MOD_RES
<222> LOCATION: (31)..(31)
<223> OTHER INFORMATION: Asn or Arg
<220> FEATURE:
<221> NAME/KEY: MOD_RES
<222> LOCATION: (34)..(34)
<223> OTHER INFORMATION: Met, Leu or Cys
<220> FEATURE:
<221> NAME/KEY: MOD_RES
<222> LOCATION: (99)..(99)
<223> OTHER INFORMATION: Ala or Thr
<220> FEATURE:
<221> NAME/KEY: MOD_RES
<222> LOCATION: (100)..(100)
<223> OTHER INFORMATION: Arg or Glu

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Xaa Xaa Tyr
            20                  25                  30

Trp Xaa Asn Trp Val Arg Gln Ala Pro Gly Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Xaa Xaa Gly Leu Asp Tyr Trp Gly Gln Gly Thr Thr Val Thr
            100                 105                 110

Val Ser Ser
        115
```

<210> SEQ ID NO 21
<211> LENGTH: 352
<212> TYPE: PRT
<213> ORGANISM: Artificial Sequence
<220> FEATURE:
<223> OTHER INFORMATION: Description of Artificial Sequence: Synthetic promyostatin (native) polypeptide

<400> SEQUENCE: 21

```
Asn Glu Asn Ser Glu Gln Lys Glu Asn Val Glu Lys Glu Gly Leu Cys
1               5                   10                  15

Asn Ala Cys Thr Trp Arg Gln Asn Thr Lys Ser Ser Arg Ile Glu Ala
            20                  25                  30

Ile Lys Ile Gln Ile Leu Ser Lys Leu Arg Leu Glu Thr Ala Pro Asn
        35                  40                  45

Ile Ser Lys Asp Val Ile Arg Gln Leu Leu Pro Lys Ala Pro Pro Leu
    50                  55                  60

Arg Glu Leu Ile Asp Gln Tyr Asp Val Gln Arg Asp Asp Ser Ser Asp
65                  70                  75                  80

Gly Ser Leu Glu Asp Asp Asp Tyr His Ala Thr Thr Glu Thr Ile Ile
                85                  90                  95

Thr Met Pro Thr Glu Ser Asp Phe Leu Met Gln Val Asp Gly Lys Pro
            100                 105                 110

Lys Cys Cys Phe Phe Lys Phe Ser Ser Lys Ile Gln Tyr Asn Lys Val
        115                 120                 125

Val Lys Ala Gln Leu Trp Ile Tyr Leu Arg Pro Val Glu Thr Pro Thr
    130                 135                 140

Thr Val Phe Val Gln Ile Leu Arg Leu Ile Lys Pro Met Lys Asp Gly
145                 150                 155                 160

Thr Arg Tyr Thr Gly Ile Arg Ser Leu Lys Leu Asp Met Asn Pro Gly
                165                 170                 175

Thr Gly Ile Trp Gln Ser Ile Asp Val Lys Thr Val Leu Gln Asn Trp
            180                 185                 190

Leu Lys Gln Pro Glu Ser Asn Leu Gly Ile Glu Ile Lys Ala Leu Asp
        195                 200                 205

Glu Asn Gly His Asp Leu Ala Val Thr Phe Pro Gly Pro Gly Glu Asp
    210                 215                 220

Gly Leu Asn Pro Phe Leu Glu Val Lys Val Thr Asp Thr Pro Lys Arg
225                 230                 235                 240

Ser Arg Arg Asp Phe Gly Leu Asp Cys Asp Glu His Ser Thr Glu Ser
                245                 250                 255

Arg Cys Cys Arg Tyr Pro Leu Thr Val Asp Phe Glu Ala Phe Gly Trp
            260                 265                 270

Asp Trp Ile Ile Ala Pro Lys Arg Tyr Lys Ala Asn Tyr Cys Ser Gly
        275                 280                 285

Glu Cys Glu Phe Val Phe Leu Gln Lys Tyr Pro His Thr His Leu Val
    290                 295                 300

His Gln Ala Asn Pro Arg Gly Ser Ala Gly Pro Cys Cys Thr Pro Thr
305                 310                 315                 320

Lys Met Ser Pro Ile Asn Met Leu Tyr Phe Asn Gly Lys Glu Gln Ile
                325                 330                 335

Ile Tyr Gly Lys Ile Pro Ala Met Val Val Asp Arg Cys Gly Cys Ser
            340                 345                 350
```

<210> SEQ ID NO 22
<211> LENGTH: 352
<212> TYPE: PRT
<213> ORGANISM: Artificial Sequence
<220> FEATURE:
<223> OTHER INFORMATION: Description of Artificial Sequence: Synthetic promyostatin (#1) polypeptide

<400> SEQUENCE: 22

Asn Glu Asn Ser Glu Gln Lys Glu Asn Val Glu Lys Glu Gly Leu Cys
1               5                   10                  15

Asn Ala Cys Thr Trp Arg Gln Asn Thr Lys Ser Ser Arg Ile Glu Ala
            20                  25                  30

Ile Lys Ile Gln Ile Leu Ser Lys Leu Arg Leu Glu Thr Ala Pro Asn
        35                  40                  45

Ile Ser Lys Asp Val Ile Arg Gln Leu Leu Pro Lys Ala Pro Pro Leu
50                  55                  60

Arg Glu Leu Ile Asp Gln Tyr Asp Val Gln Arg Asp Asp Ser Ser Asp
65                  70                  75                  80

Gly Ser Leu Glu Asp Asp Asp Tyr His Ala Thr Thr Glu Thr Ile Ile
                85                  90                  95

Thr Met Pro Thr Glu Ser Asp Phe Leu Met Gln Val Asp Gly Lys Pro
            100                 105                 110

Lys Cys Cys Phe Phe Lys Phe Ser Ser Lys Ile Gln Tyr Asn Lys Val
        115                 120                 125

Val Lys Ala Gln Leu Trp Ile Tyr Leu Arg Pro Val Glu Thr Pro Thr
130                 135                 140

Thr Val Phe Val Gln Ile Leu Arg Leu Ile Lys Pro Met Lys Asp Gly
145                 150                 155                 160

Thr Arg Tyr Thr Gly Ile Arg Ser Leu Lys Leu Asp Met Asn Pro Gly
                165                 170                 175

Thr Gly Ile Trp Gln Ser Ile Asp Val Lys Thr Val Leu Gln Asn Trp
            180                 185                 190

Leu Lys Gln Pro Glu Ser Asn Leu Gly Ile Glu Ile Lys Ala Leu Asp
        195                 200                 205

Glu Asn Gly His Asp Leu Ala Val Thr Phe Pro Gly Pro Gly Glu Asp
210                 215                 220

Gly Leu Asn Pro Phe Leu Glu Val Lys Val Thr Asp Thr Pro Lys Arg
225                 230                 235                 240

Ser Arg Arg Asn Leu Gly Leu Asp Cys Asp Glu His Ser Ser Glu Ser
                245                 250                 255

Arg Cys Cys Arg Tyr Pro Leu Thr Val Asp Phe Glu Ala Phe Gly Trp
            260                 265                 270

Asp Trp Ile Ile Ala Pro Lys Arg Tyr Lys Ala Asn Tyr Cys Ser Gly
        275                 280                 285

Glu Cys Glu Phe Val Phe Leu Gln Lys Tyr Pro His Thr His Leu Val
290                 295                 300

His Gln Ala Asn Pro Arg Gly Ser Ala Gly Pro Cys Cys Thr Pro Thr
305                 310                 315                 320

Lys Met Ser Pro Ile Asn Met Leu Tyr Phe Asn Gly Lys Glu Gln Ile
                325                 330                 335

Ile Tyr Gly Lys Ile Pro Ala Met Val Val Asp Arg Cys Gly Cys Ser
            340                 345                 350

<210> SEQ ID NO 23
<211> LENGTH: 352

```
<212> TYPE: PRT
<213> ORGANISM: Artificial Sequence
<220> FEATURE:
<223> OTHER INFORMATION: Description of Artificial Sequence: Synthetic
      promyostatin (#2) polypeptide

<400> SEQUENCE: 23

Asn Glu Asn Ser Glu Gln Lys Glu Asn Val Glu Lys Glu Gly Leu Cys
1               5                   10                  15

Asn Ala Cys Thr Trp Arg Gln Asn Thr Lys Ser Ser Arg Ile Glu Ala
            20                  25                  30

Ile Lys Ile Gln Ile Leu Ser Lys Leu Arg Leu Glu Thr Ala Pro Asn
        35                  40                  45

Ile Ser Lys Asp Val Ile Arg Gln Leu Leu Pro Lys Ala Pro Pro Leu
50                  55                  60

Arg Glu Leu Ile Asp Gln Tyr Asp Val Gln Arg Asp Asp Ser Ser Asp
65                  70                  75                  80

Gly Ser Leu Glu Asp Asp Asp Tyr His Ala Thr Thr Glu Thr Ile Ile
                85                  90                  95

Thr Met Pro Thr Glu Ser Asp Phe Leu Met Gln Val Asp Gly Lys Pro
            100                 105                 110

Lys Cys Cys Phe Phe Lys Phe Ser Ser Lys Ile Gln Tyr Asn Lys Val
        115                 120                 125

Val Lys Ala Gln Leu Trp Ile Tyr Leu Arg Pro Val Glu Thr Pro Thr
130                 135                 140

Thr Val Phe Val Gln Ile Leu Arg Leu Ile Lys Pro Met Lys Asp Gly
145                 150                 155                 160

Thr Arg Tyr Thr Gly Ile Arg Ser Leu Lys Leu Asp Met Asn Pro Gly
                165                 170                 175

Thr Gly Ile Trp Gln Ser Ile Asp Val Lys Thr Val Leu Gln Asn Trp
            180                 185                 190

Leu Lys Gln Pro Glu Ser Asn Leu Gly Ile Glu Ile Lys Ala Leu Asp
        195                 200                 205

Glu Asn Gly His Asp Leu Ala Val Thr Phe Pro Gly Pro Gly Glu Asp
210                 215                 220

Gly Leu Asn Pro Phe Leu Glu Val Lys Val Thr Asp Thr Pro Lys Arg
225                 230                 235                 240

Ser Arg Arg Asp Phe Gly Leu Asp Cys Asp Glu His Ser Thr Glu Ser
                245                 250                 255

Arg Cys Cys Arg Tyr Pro Leu Thr Val Asp Phe Glu Ala Phe Gly Trp
            260                 265                 270

Asp Trp Ile Ile Ala Pro Lys Arg Tyr Lys Ala Asn Tyr Cys Ser Gly
        275                 280                 285

Gln Cys Glu Tyr Met Phe Met Gln Lys Tyr Pro His Thr His Leu Val
290                 295                 300

His Gln Ala Asn Pro Arg Gly Ser Ala Gly Pro Cys Cys Thr Pro Thr
305                 310                 315                 320

Lys Met Ser Pro Ile Asn Met Leu Tyr Phe Asn Gly Lys Glu Gln Ile
                325                 330                 335

Ile Tyr Gly Lys Ile Pro Ala Met Val Val Asp Arg Cys Gly Cys Ser
            340                 345                 350

<210> SEQ ID NO 24
<211> LENGTH: 352
<212> TYPE: PRT
<213> ORGANISM: Artificial Sequence
```

```
<220> FEATURE:
<223> OTHER INFORMATION: Description of Artificial Sequence: Synthetic
      promyostatin (#3) polypeptide

<400> SEQUENCE: 24

Asn Glu Asn Ser Glu Gln Lys Glu Asn Val Glu Lys Glu Gly Leu Cys
1               5                   10                  15

Asn Ala Cys Thr Trp Arg Gln Asn Thr Lys Ser Ser Arg Ile Glu Ala
            20                  25                  30

Ile Lys Ile Gln Ile Leu Ser Lys Leu Arg Leu Glu Thr Ala Pro Asn
        35                  40                  45

Ile Ser Lys Asp Val Ile Arg Gln Leu Leu Pro Lys Ala Pro Pro Leu
    50                  55                  60

Arg Glu Leu Ile Asp Gln Tyr Asp Val Gln Arg Asp Asp Ser Ser Asp
65                  70                  75                  80

Gly Ser Leu Glu Asp Asp Asp Tyr His Ala Thr Thr Glu Thr Ile Ile
                85                  90                  95

Thr Met Pro Thr Glu Ser Asp Phe Leu Met Gln Val Asp Gly Lys Pro
            100                 105                 110

Lys Cys Cys Phe Phe Lys Phe Ser Ser Lys Ile Gln Tyr Asn Lys Val
        115                 120                 125

Val Lys Ala Gln Leu Trp Ile Tyr Leu Arg Pro Val Glu Thr Pro Thr
    130                 135                 140

Thr Val Phe Val Gln Ile Leu Arg Leu Ile Lys Pro Met Lys Asp Gly
145                 150                 155                 160

Thr Arg Tyr Thr Gly Ile Arg Ser Leu Lys Leu Asp Met Asn Pro Gly
                165                 170                 175

Thr Gly Ile Trp Gln Ser Ile Asp Val Lys Thr Val Leu Gln Asn Trp
            180                 185                 190

Leu Lys Gln Pro Glu Ser Asn Leu Gly Ile Glu Ile Lys Ala Leu Asp
        195                 200                 205

Glu Asn Gly His Asp Leu Ala Val Thr Phe Pro Gly Pro Gly Glu Asp
    210                 215                 220

Gly Leu Asn Pro Phe Leu Glu Val Lys Val Thr Asp Thr Pro Lys Arg
225                 230                 235                 240

Ser Arg Arg Asp Phe Gly Leu Asp Cys Asp Glu His Ser Thr Glu Ser
                245                 250                 255

Arg Cys Cys Arg Tyr Pro Leu Thr Val Asp Phe Glu Ala Phe Gly Trp
            260                 265                 270

Asp Trp Ile Ile Ala Pro Lys Arg Tyr Lys Ala Asn Tyr Cys Ser Gly
        275                 280                 285

Glu Cys Glu Phe Val Phe Leu Gln Lys Tyr Pro His Thr His Leu Val
    290                 295                 300

His Gln Ala Asn Pro Arg Gly Ser Ala Gly Pro Cys Cys Thr Pro Thr
305                 310                 315                 320

Lys Met Ser Pro Ile Asn Met Leu Tyr Phe Asn Asp Lys Gln Gln Ile
                325                 330                 335

Ile Tyr Gly Lys Ile Pro Gly Met Val Val Asp Arg Cys Gly Cys Ser
            340                 345                 350

<210> SEQ ID NO 25
<211> LENGTH: 109
<212> TYPE: PRT
<213> ORGANISM: Homo sapiens

<400> SEQUENCE: 25
```

```
Asp Phe Gly Leu Asp Cys Asp Glu His Ser Thr Glu Ser Arg Cys Cys
1               5                   10                  15

Arg Tyr Pro Leu Thr Val Asp Phe Glu Ala Phe Gly Trp Asp Trp Ile
                20                  25                  30

Ile Ala Pro Lys Arg Tyr Lys Ala Asn Tyr Cys Ser Gly Glu Cys Glu
                35                  40                  45

Phe Val Phe Leu Gln Lys Tyr Pro His Thr His Leu Val His Gln Ala
    50                  55                      60

Asn Pro Arg Gly Ser Ala Gly Pro Cys Cys Thr Pro Thr Lys Met Ser
65                  70                  75                  80

Pro Ile Asn Met Leu Tyr Phe Asn Gly Lys Gln Ile Ile Tyr Gly
                85                  90                  95

Lys Ile Pro Ala Met Val Val Asp Arg Cys Gly Cys Ser
                100                 105

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
                20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg
                20                  25                  30

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asn Tyr Trp Met Asn
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 29

Asn Tyr Trp Cys Asn
1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Tyr Trp Met Asn
1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asn Tyr Trp Leu Asn
1               5

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Trp Val Arg Gln Ala Pro Gly Lys Gly Leu Glu Trp Val Ala
1               5                   10

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Ile Arg Leu Lys Ser Asp Asn Tyr Ala Thr His Tyr Ala Glu Ser
1               5                   10                  15

Val Lys Gly

<210> SEQ ID NO 34
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30
```

<210> SEQ ID NO 35
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Thr Glu
            20                  25                  30

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Leu Asp Tyr
1

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Trp Gly Gln Gly Thr Thr Val Thr Val Ser Ser
1               5                   10

<210> SEQ ID NO 38
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Lys Ala Ser Gln Asp Ile Asn Lys Tyr Val Ala
1               5                   10

<210> SEQ ID NO 40

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Trp Tyr Gln Gln Lys Pro Gly Lys Ala Pro Lys Leu Leu Ile Tyr
1               5                   10                  15

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Tyr Thr Ser Thr Leu Gln Pro
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Thr Ser Phe Leu Gln Pro
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Tyr Thr Ser Trp Leu Gln Pro
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Tyr Thr Lys Thr Leu Gln Pro
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45
```

Tyr Thr Arg Thr Leu Gln Pro
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Tyr Thr Ser His Leu Gln Pro
1               5

<210> SEQ ID NO 47
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Gln Tyr Asp Asn Leu Leu Tyr Thr
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Leu Gln Tyr Asp Ala Leu Leu Tyr Thr
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Leu Gln Tyr Asp Asn Lys Leu Tyr Thr
1               5

<210> SEQ ID NO 51
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Phe Gly Gln Gly Thr Lys Leu Glu Ile Lys
1               5                   10

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Cys Pro Ser Cys Pro
1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Cys Pro Pro Cys Pro
1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Glu Phe Val Phe Leu Gln
1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Glu Tyr Met Phe Met Gln
1               5
```

ANTIBODIES THAT BIND MYOSTATIN, COMPOSITIONS AND METHODS

CROSS-REFERENCE TO RELATED APPLICATIONS

This application claims the benefit under 35 U.S.C. §119 of U.S. Provisional Application Ser. No. 61/374,095, filed Aug. 16, 2010, which is hereby incorporated by reference.

SEQUENCE LISTING

The instant application contains a Sequence Listing which has been submitted in ASCII format via EFS-Web and is hereby incorporated by reference in its entirety. Said ASCII copy, created on Sep. 18, 2013, is named 22094US$_{13}$CRF$_{13}$sequencelisting.txt and is 44,594 bytes in size.

FIELD OF THE INVENTION

The present invention relates in general to myostatin and to proteins that bind thereto. In particular, the invention relates to myostatin inhibitors, and uses thereof.

BACKGROUND OF THE INVENTION

Growth/differentiation factor 8 (GDF-8), also referred to as myostatin, is a TGF-β family member expressed for the most part in the cells of developing and adult skeletal muscle tissue. Myostatin appears to play an essential role in negatively controlling skeletal muscle growth (McPherron et al. Nature (London) 387, 83-90 (1997)). Mutations in the myostatin gene have been demonstrated in various species, including cattle, pigs, dogs and humans, and have resulted in increased musculature (Kocamis and Killefer, Domestic Animal Endocrinology 23:447; 2002). Moreover, antagonizing myostatin has been shown to increase lean muscle mass in animals (McFerron et al, supra, Zimmers et al, Science 296: 1486 (2002)).

Myostatin antagonists have also been evaluated in human clinical trials. A human antibody referred to as MYO-29 was evaluated in patients with various forms of muscular dystrophy. Early clinical results with this myostatin antagonist demonstrated good safety and tolerability, with no noted improvements in muscle strength or function (however, the study was not powered to demonstrate efficacy); a trend toward increased muscle size was noted in a limited number of subjects (Wagner et al. Ann. Neurol. 63:561; 2008). In subsequent reports, overall quantitative muscle strength measurements in treated patients did not improve, however several patients exhibited improvement in single muscle fiber contractile properties (Krivickas et al. Muscle Nerv. 39:3; 2009).

Regulation of the myostatin pathway is believed to require processing of a latent myostatin complex into mature myostatin. The latent complex is formed of a cleaved propeptide domain that is noncovalently associated with a mature C-terminal dimer, and is biologically inactive. Tissue-specific factors are thought to be responsible for converting the inactive complex into the biologically active form. Myostatin also forms a complex with follistatin-related gene (FLRG) and growth and differentiation-associated factor-associated serum protein-1 (GASP-1), both of which complexes have been identified in serum.

Mature myostatin binds with high affinity to the activin type IIB receptor (ActRIIB), and with lesser affinity to the activin receptor (ActRIIA). Intracellular signalling is initiated by binding of dimeric myostatin to ActRIIB followed by recruitment of a low-affinity type I receptor, either activin-like kinase 4 (ALK4) or activin-like kinase 5 (ALK5). Phosphorylation of the type I receptor results in initiation of the intracellular signalling pathway that is responsible for myostatin's biological effects.

Utility of myostatin antagonists in vivo has been complicated not only by the nature of regulation and signalling of the myostatin pathway but also by the high degree of similarity of myostatin to growth and differentiation factor 11 (GDF-11; also known as bone morphogenetic protein 11 or BMP-11), which is 90% identical to myostatin at the amino acid level, in the active domain. While the high degree of sequence identity and similarities in signalling mechanism suggest that myostatin and GDF-11 share certain functions, targeted gene disruptions of these two TGF-beta family members show very different results. Myostatin knockout mice exhibit hyperplasia and hypertrophy of myofibers, and GDF-11 knockout mice die shortly after birth with numerous abnormalities; dual knockout animals show additional abnormalities not seen in single knockout mice (McPherron et al., BMC Dev Biol. 9: 24; 2009).

Accordingly, there is a further need in the art for agents that bind myostatin and antagonize its activity while eliminating or minimizing adverse effects of inhibiting this and related pathways.

SUMMARY OF THE INVENTION

Figure 1:
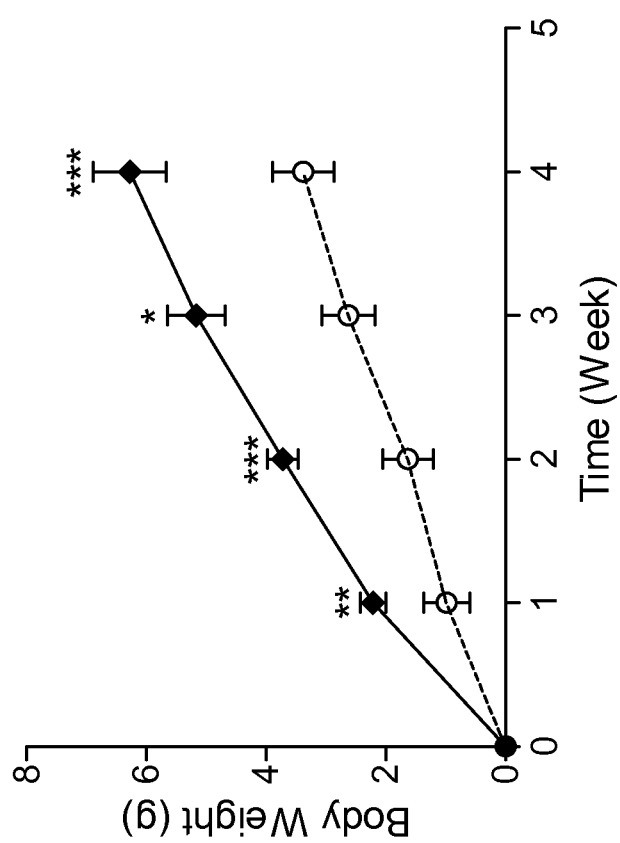
FIG. 1 illustrates the increase in total body weight of mice given a myostatin inhibitor (anti-myostatin antibody 12A5-5, solid diamonds) as compared with a control (PBS; open circles), as described in Example 4.

The invention provides an isolated myostatin-specific antibody that binds myostatin with a $K_d$ of less than 100 pM. In one embodiment, the invention provides an isolated myostatin-specific antibody that binds myostatin with a $K_d$ of less than 100 pM and binds GDF-11 with a $K_d$ of greater than 10 nM. In another embodiment, the invention provides an isolated myostatin-specific antibody that binds myostatin with an affinity at least 5,000 times greater than its affinity for GDF-11. In a further embodiment, the invention provides an isolated myostatin-specific antibody that exhibits selectivity for myostatin that is at least 5,000 times greater than for GDF-11.

In one aspect of the invention, there is provided an isolated myostatin-specific antibody that binds myostatin and blocks the interaction of myostatin with ALK4. In another aspect, there is provided an isolated myostatin-specific antibody that binds myostatin and blocks the interaction of myostatin with ALK4 but co-binds with a myostatin/ActRIIA complex and/or a myostatin/ActRIIB complex.

In another aspect of the invention, there is provided an isolated myostatin-specific antibody that binds myostatin, wherein two regions in myostatin that are required for binding of myostatin to the myostatin-specific antagonist locate at sequence near position 21 to 31 and position 50 to 60 of mature myostatin (SEQ ID NO:25). Also provided is an isolated myostatin-specific antibody that interacts with two regions in myostatin, located at sequence near position 21 to 31 and position 50 to 60 of mature myostatin, so as to prevent chymotrypsin cleavage of peptide bonds within these regions.

In one embodiment of the invention, the myostatin-specific antagonist is an antibody comprising at least one light chain and at least one heavy chain, wherein the light chain comprises a constant region and a variable region that comprises three complementarity determining regions (CDRs) and the heavy chain comprises a constant region and a variable region that comprises three complementarity determining regions (CDRs). This embodiment may incorporate one or more of the previously described embodiments and/or aspects of the invention. In certain embodiments, the sequences of the heavy and light chain CDRs are as disclosed herein. In one embodiment, the light chain CDRs are those disclosed in SEQ ID NO:10, and the heavy chain CDRs are those disclosed in SEQ ID NO:20. In another embodiment, the light chain CDRs are selected from the group consisting of the light chain CDRs disclosed in SEQ ID NO:1; the light chain CDRs disclosed in SEQ ID NO:2; the light chain CDRs disclosed in SEQ ID NO:3; the light chain CDRs disclosed in SEQ ID NO:4; the light chain CDRs disclosed in SEQ ID NO:5; the light chain CDRs disclosed in SEQ ID NO:6; the light chain CDRs disclosed in SEQ ID NO:7; the light chain CDRs disclosed in SEQ ID NO:8; and the light chain CDRs disclosed in SEQ ID NO:9; and the heavy chain CDRs are selected from the group consisting of: the heavy chain CDRs disclosed in SEQ ID NO:11; the heavy chain CDRs disclosed in SEQ ID NO:12; the heavy chain CDRs disclosed in SEQ ID NO:13; the heavy chain CDRs disclosed in SEQ ID NO:14; the heavy chain CDRs disclosed in SEQ ID NO:15; the heavy chain CDRs disclosed in SEQ ID NO:16; the heavy chain CDRs disclosed in SEQ ID NO:17; the heavy chain CDRs disclosed in SEQ ID NO:18; and the heavy chain CDRs disclosed in SEQ ID NO:19.

In certain embodiments, the sequences of the heavy and light chain variable regions are as disclosed herein. In one embodiment, the light chain the light chain variable region comprises the amino acid sequence set forth in SEQ ID NO:10, and the heavy chain variable region comprises the amino acid sequence set forth in SEQ ID NO:20. In another embodiment, the light chain variable region is selected from the group consisting of the light chain variable region disclosed in SEQ ID NO:1; the light chain variable region disclosed in SEQ ID NO:2; the light chain variable region disclosed in SEQ ID NO:3; the light chain variable region disclosed in SEQ ID NO:4; the light chain variable region disclosed in SEQ ID NO:5; the light chain variable region disclosed in SEQ ID NO:6; the light chain variable region disclosed in SEQ ID NO:7; the light chain variable region disclosed in SEQ ID NO:8; and the light chain variable region disclosed in SEQ ID NO:9; and the heavy chain variable region is selected from the group consisting of: the heavy chain variable region disclosed in SEQ ID NO:11; the heavy chain variable region disclosed in SEQ ID NO:12; the heavy chain variable region disclosed in SEQ ID NO:13; the heavy chain variable region disclosed in SEQ ID NO:14; the heavy chain variable region disclosed in SEQ ID NO:15; the heavy chain variable region disclosed in SEQ ID NO:16; the heavy chain variable region disclosed in SEQ ID NO:17; the heavy chain variable region disclosed in SEQ ID NO:18; and the heavy chain variable region disclosed in SEQ ID NO:19.

Variants of the afore-mentioned antibodies are also provided. In one embodiment a variant antibody is 90%, 91%, 92%, 93%, 94%, 95%, 96%, 97%, 98%, or 99% identical to one of the antibodies, for example, antibody 12A5-5. In another embodiment, a variant antibody differs from the aforementioned antibodies (for example, 12A5-5) at one, two, three, four fine, six, seven, eight, nine or ten amino acid residues (by substitution or deletion of the amino acid(s). In a further embodiment, one (or more) amino acid is modified post-translationally (for example, by cyclization or conversion to another amino acid; and/or by deamidation, isomerization, glycation and/or oxidation).

In a further aspect of the invention, the antibody light chain constant region is selected from the group consisting of a kappa and a lambda light chain, and the heavy chain constant region is selected from the group consisting of a mu, a delta, a gamma, an alpha, and an epsilon constant region. A further embodiment provides an antibody that antibody belongs to a subclass selected from the group consisting of IgG1, IgG2, IgG3 and IgG4. It is understood that these aspects of the invention apply equally to the previously described aspects and embodiments.

The invention also provides isolated nucleic acid encoding any of the afore-mentioned myostatin-specific antagonists, as well as a vector comprising such nucleic acid, an isolated host cell transfected or transformed with such vector, and a method for the production of a myostatin-specific antagonist comprising culturing such a host cell under conditions promoting expression and recovering the myostatin-specific antagonist from the culture medium. A composition comprising the myostatin-specific antagonist as previously described and a physiologically acceptable diluent, excipient or carrier is also provided, as is method of inhibiting at least one activity of myostatin, comprising administering such a composition to an individual such that at least one activity of myostatin is partially or fully inhibited.

In additional embodiments of the invention, the individual is afflicted with a condition selected from the group consisting of: hypogonadism (including hypogonadism resulting from androgen deprivation therapy, and hypogonadism resulting from age-related decrease in gonadal functioning), cachexia; cardiac cachexia, renal cachexia, cardiac atrophy; cardiac hypotrophy; heat failure; sarcopenia; traumatic bone fracture; osteoporotic fracture; bone loss (for example, osteoporosis or osteopenia); Addison's disease; amyotrophic lateral sclerosis or motor neuron disease (ALS; MND; Lou Gehrig's disease); Bell's palsy (and/or facial nerve problems); botulism; cerebral palsy; Charcot-Marie-Tooth disease and other peripheral neuropathies; Cushing's syndrome; diabetic neuropathy; Guillan-Barre syndrome; multiple sclerosis; muscular atrophy (including progressive and spinal muscular atrophy); muscular dystrophy (of which there are numerous forms; including Becker's muscular dystrophy, congenital muscular dystrophy, Duchenne muscular dystrophy, distal muscular dystrophy, Emery-Dreifuss muscular dystrophy, facioscapulohumeral muscular dystrophy, limb-girdle muscular dystrophy, myotonic muscular dystrophy, oculopharyngeal muscular dystrophy, spinal muscular atrophy, Brown-Vialetto-Van Laere syndrome (BVVL), Fazio-Londe (FL) syndrome, and other syndromes characterized by progressive skeletal muscle weakness, defects in muscle proteins, and the death of muscle cells and tissue); myasthenia gravis; poliomyelitis; polymyositis; sprains and strains of muscles, tendons and/or ligaments; stroke (and other conditions that result in muscle wasting, such as prolonged inactivity or bed-rest, immobilization of limbs [for example, by casting and/or splinting] and space flight); and conditions treatable by growth hormone, insulin growth factor-1 (IGF-1), growth hormone secretagogues, and other agents related to the growth hormone-IGF-1 axis.

DETAILED DESCRIPTION OF THE INVENTION

The present invention provides compositions, kits, and methods relating to molecules that bind to myostatin (such as anti-myostatin antibodies, antibody fragments, and antibody derivatives), and inhibit at least on biological activity of myostatin. As used herein the term "myostatin antagonist" is used interchangeably with "myostatin inhibitor". A myostatin antagonist according to the present invention inhibits or blocks at least one activity of myostatin, or alternatively, blocks expression of myostatin or its receptor. Inhibiting or blocking myostatin activity can be achieved, for example, by employing one or more inhibitory agents which interfere with the binding of myostatin to its receptor, and/or blocks signal transduction resulting from the binding of myostatin to its receptor. Antagonists include agents that bind to myostatin itself, or agents that bind to a myostatin receptor. For example, myostatin antagonists include but are not limited to follistatin, the myostatin prodomain, growth and differentiation factor 11 (GDF-11) prodomain, prodomain fusion proteins, antagonistic antibodies that bind to myostatin, antagonistic antibodies or antibody fragments that bind to the activin type IIB receptor, soluble activin type IIB receptor, soluble activin type IIB receptor fusion proteins, soluble myostatin analogs (soluble ligands), oligonucleotides, small molecules, peptidomimetics, and myostatin binding agents. These are described in more detail below.

Also provided are nucleic acids, and derivatives and fragments thereof, comprising a sequence of nucleotides that encodes all or a portion of a polypeptide that binds to myostatin, e.g., a nucleic acid encoding all or part of an anti-myostatin antibody, antibody fragment, or antibody derivative; plasmids and vectors comprising such nucleic acids, and cells or cell lines comprising such nucleic acids and/or vectors and plasmids. The provided methods include, for example, methods of making, identifying, or isolating molecules that bind to myostatin, such as anti-myostatin antibodies, methods of determining whether a molecule binds to myostatin, methods of determining whether a molecule antagonizes myostatin, methods of making compositions, such as pharmaceutical compositions, comprising a molecule that binds to myostatin, and methods for administering a molecule that binds myostatin to a subject, for example, methods for treating a condition mediated by myostatin, and for antagonizing (or inhibiting) a biological activity of myostatin, in vivo or in vitro. One such biological activity of myostatin is binding to myostatin receptor; another such activity is the negative regulation of skeletal muscle growth.

Polynucleotide and polypeptide sequences are indicated using standard one- or three-letter abbreviations. Unless otherwise indicated, each polypeptide sequence has amino termini at the left and a carboxy termini at the right; each single-stranded nucleic acid sequence, and the top strand of each double-stranded nucleic acid sequence, has a 5' termini at the left and a 3' termini at the right. A particular polypeptide or polynucleotide sequence also can be described by explaining how it differs from a reference sequence.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The following terms, unless otherwise indicated, shall be understood to have the following meanings:

The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature without human intervention. Thus, a molecule that is chemically synthesized, or synthesized in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The terms "myostatin inhibitor" and "myostatin antagonist" are used interchangeably. Each is a molecule that detectably inhibits at least one function of myostatin. Conversely, a "myostatin agonist" is a molecule that detectably increases at least one function of myostatin. The inhibition caused by a myostatin inhibitor need not be complete so long as it is detectable, for example by using an assay. Any assay of a function of myostatin can be used, examples of which are provided herein. Examples of functions of myostatin that can be inhibited by a myostatin inhibitor (or increased by a myostatin agonist) include binding to a myostatin receptor (or cells expressing such a receptor), and the negative regulation of skeletal muscle growth. Examples of types of myostatin inhibitors and myostatin agonists include, but are not limited to, myostatin binding polypeptides such as antigen binding proteins (e.g., myostatin antigen binding proteins), antibodies, antibody fragments, and antibody derivatives.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

The term "polypeptide fragment" as used herein refers to a polypeptide that has an amino-terminal and/or carboxy-terminal deletion as compared to a corresponding full-length protein. Fragments can be, for example, at least 5, 6, 7, 8, 9, 10, 11, 12, 13, 14, 15, 20, 50, 70, 80, 90, 100, 150 or 200 amino acids in length. Fragments can also be, for example, at most 1,000, 750, 500, 250, 200, 175, 150, 125, 100, 90, 80, 70, 60, 50, 40, 30, 20, 15, 14, 13, 12, 11, or 10 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence or a tag protein).

Polypeptides of the invention include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (4) confer or modify other physicochemical or functional properties. Analogs include muteins of a polypeptide. For example, single or multiple amino acid substitutions (e.g., conservative amino acid substitutions) may be made in the naturally occurring sequence (e.g., in the portion of the polypeptide outside the domain(s) forming intermolecular contacts). Consensus sequences can be used to select amino acid residues for substitution; those of skill in the art recognize that additional amino acid residues may also be substituted.

A "conservative amino acid substitution" is one that does not substantially change the structural characteristics of the parent sequence (e.g., a replacement amino acid should not tend to break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991), which are each incorporated herein by reference.

The present invention also provides non-peptide analogs of myostatin binding polypeptides. Non-peptide analogs are commonly used in the pharmaceutical industry as drugs with properties analogous to those of the template peptide. These types of non-peptide compound are termed "peptide mimetics" or "peptidomimetics," see, for example, Fauchere, J. Adv. Drug Res. 15:29 (1986); Veber and Freidinger TINS p. 392 (1985); and Evans et al. J. Med. Chem. 30:1229 (1987), which are incorporated herein by reference. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a desired biochemical property or pharmacological activity), such as a human antibody, but have one or more peptide linkages optionally replaced by a linkage selected from the group consisting of: —CH$_2$NH—, —CH$_2$S—, —CH$_2$—CH$_2$—, —CH=CH-(cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992), incorporated herein by reference), for example, by adding internal cysteine residues capable of forming intramolecular disulfide bridges which cyclize the peptide.

A "variant" of a polypeptide (e.g., an antibody) comprises an amino acid sequence wherein one or more amino acid residues are inserted into, deleted from and/or substituted into the amino acid sequence relative to another polypeptide sequence. Variants of the invention include fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and/or glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129; Roque et al., 2004, Biotechnol. Prog. 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively; IgG antibodies can be further divided into four subclasses in humans (IgG1, IgG2, IgG3 and IgG4). Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in *Sequences of Proteins of Immunological Interest, 5th* Ed., US Dept. of Health and Human Services, PHS, NIH, NIH Publication no. 91-3242, 1991. Other numbering systems for the amino acids in immunoglobulin chains include IMGT® (the international ImMunoGeneTics information system; Lefranc et al, *Dev. Comp. Immunol.* 29:185-203; 2005) and AHo (Honegger and Pluckthun, *J. Mol. Biol.* 309(3):657-670; 2001).

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific." Monospecfic antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, variable region fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_H1$ domains; a F(ab')$_2$ fragment is a bivalent fragment having two Fab fragments linked by a disulfide bridge at the hinge region; a Fd fragment has the $V_H$ and $C_H1$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634, 6,696,245, US App. Pub. No. 05/0202512, 04/0202995, 04/0038291, 04/0009507, 03/0039958, Ward et al., Nature 341:544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, Science 242:423-26 and Huston et al., 1988, Proc. Natl. Acad. Sci. USA 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48, and Poljak et al., 1994, Structure 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, triabodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. supra; Lefranc et al., supra and/or Honegger and Pluckthun, supra. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-myostatin antibody. In another embodiment, all of the CDRs are derived from a human anti-myostatin antibody. In another embodiment, the CDRs from more than one human anti-myostatin antibodies are mixed and matched in a chimeric antibody. For instance, a chimeric antibody may comprise a CDR1 from the light chain of a first human anti-myostatin antibody, a CDR2 and a CDR3 from the light chain of a second human anti-myostatin antibody, and the CDRs from the heavy chain from a third anti-myostatin antibody. Other combinations are possible and are included within the embodiments of the invention.

Further, the framework regions may be derived from one of the same anti-myostatin antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind myostatin). See, e.g., U.S. Pat. No. 4,816,567 and Morrison, 1985, Science 229:1202-07.

A "neutralizing antibody" or an "inhibitory antibody" is an antibody that inhibits the interaction of myostatin with a myostatin receptor when an excess of the anti-myostatin antibody reduces the amount of interaction by at least about 20% using an assay such as those described herein in the Examples. In various embodiments, the antigen binding protein reduces the interaction of myostatin with a myostatin receptor by at least 30%, 40%, 50%, 60%, 70%, 75%, 80%, 85%, 90%, 95%, 97%, 99%, and 99.9%.

Fragments or analogs of antibodies can be readily prepared by those of ordinary skill in the art following the teachings of this specification and using techniques well-known in the art. Amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, e.g., Bowie et al., 1991, Science 253:164.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human myostatin) if it binds to the antigen with a dissociation constant ($K_d$) of 1 nanomolar or less. An antigen binding protein may also bind "selectively" or "preferentially" to one antigen as compared to a second antigen when the dissociation constant for the first antigen is significantly lower than the dissociation constant for the second antigen. "Selectivity" refers to the degree to which an antigen binding protein binds to a particular antigen as compared to the degree to which it binds a second antigen, for example, a highly related antigen. For example, a "myostatin-specific antagonist" is one that binds myostatin with a $K_d$ of one nanomolar or less, and binds to GDF-11 with a $K_d$ of 10 nM or more. Thus, the selectivity of a myostatin antagonist for myostatin versus GDF-11 may be ten-fold, or greater.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by (or interacts with) an antigen binding protein (e.g., an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by, or interact with, an antigen binding protein).

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof, of the invention.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06.

A "host cell" is a cell that can be used to express a nucleic acid, e.g., a nucleic acid of the invention. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, Cell 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31) or CHO strain DX-B11, which is deficient in DHFR (see Urlaub et al., 1980, Proc. Natl. Acad. Sci. USA 77:4216-20), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Antigen Binding Proteins

In one aspect, the present invention provides antigen binding proteins (e.g., antibodies, antibody fragments, antibody derivatives, antibody muteins, and antibody variants) that bind to myostatin, e.g., human myostatin.

Antigen binding proteins in accordance with the present invention include antigen binding proteins that inhibit a biological activity of myostatin. Examples of such biological activities include binding of myostatin to a myostatin receptor, and binding to cells expressing such a myostatin receptor. Other biological activities include those mediated by myostatin in vivo, such as negative regulation of skeletal muscle growth.

Different antigen binding proteins may bind to different domains or epitopes of myostatin or act by different mechanisms of action. Examples include but are not limited to antigen binding proteins that interfere with the ability of myostatin to a myostatin receptor, or a subunit thereof. An antigen binding protein need not completely inhibit myostatin induced activity to find use in the present invention; rather, antigen binding proteins that reduce a particular activity of myostatin are contemplated for use as well. (Discussions herein of particular mechanisms of action for myostatin-binding antigen binding proteins in treating particular diseases are illustrative only, and the methods presented herein are not bound thereby.)

Other derivatives of anti-myostatin antibodies within the scope of this invention include covalent or aggregative conjugates of anti-myostatin antibodies, or fragments thereof, with other proteins or polypeptides, such as by expression of recombinant fusion proteins comprising heterologous polypeptides fused to the N-terminus or C-terminus of an anti-myostatin antibody polypeptide. For example, the conjugated peptide may be a heterologous signal (or leader) polypeptide, e.g., the yeast alpha-factor leader, or a peptide such as an epitope tag. Antigen binding protein-containing fusion proteins can comprise peptides added to facilitate purification or identification of antigen binding protein (e.g., a tag protein, such as poly-His). An antigen binding protein also can be linked to the FLAG® peptide as described in Hopp et al., Bio/Technology 6:1204, 1988, and U.S. Pat. No. 5,011, 912. The FLAG® peptide is highly antigenic and provides an epitope reversibly bound by a specific monoclonal antibody (mAb), enabling rapid assay and facile purification of expressed recombinant protein. Reagents useful for preparing fusion proteins in which the FLAG® peptide is fused to a given polypeptide are commercially available (Sigma-Aldrich, St. Louis Mo.).

Oligomers that contain one or more antigen binding proteins may be employed as myostatin antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have myostatin binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 "Construction of Immunoglobulin Fusion Proteins", in *Current Protocols in Immunology, Suppl.* 4, pages 10.19.1-10.19.11.

One embodiment of the present invention is directed to a dimer comprising two fusion proteins created by fusing a myostatin binding fragment of an anti-myostatin antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of an anti-myostatin antibody may be substituted for the variable portion of an antibody heavy and/or light chain.

Alternatively, the oligomer is a fusion protein comprising multiple antigen binding proteins, with or without peptide linkers (spacer peptides). Among the suitable peptide linkers are those described in U.S. Pat. Nos. 4,751,180 and 4,935,233.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191, hereby incorporated by reference. The use of a modified leucine zipper that allows for stable trimerization of a heterologous protein fused thereto is described in Fanslow et al., 1994, Semin. Immunol. 6:267-78. In one approach, recombinant fusion proteins comprising an anti-myostatin antibody fragment or derivative fused to a leucine zipper peptide are expressed in suitable host cells, and the soluble oligomeric anti-myostatin antibody fragments or derivatives that form are recovered from the culture supernatant.

In one aspect, the present invention provides antigen binding proteins that interfere with the binding of myostatin to a myostatin receptor, or subunit thereof. For example, an antigen binding protein may block the interaction of myostatin with ALK4, but may co-bind with myostatin complexed with ActRIIB and/or myostatin complexed with ActRIIA. Such antigen binding proteins can be made against myostatin, or a fragment, variant or derivative thereof, and screened in conventional assays for the ability to interfere with a myostatin receptor (or cells expressing such a receptor). Examples of suitable assays are assays that test the antigen binding proteins for the ability to inhibit binding of myostatin to cells expressing a myostatin receptor, or that test antigen binding proteins for the ability to reduce a biological or cellular response that results from the interaction of such receptor(s) and myostatin (i.e., cell-based assays, and in vitro binding assays, such as those described herein in the Examples). Additional assays that test the antigen binding proteins include those that qualitatively or quantitatively compare the binding of an antigen binding protein to a myostatin polypeptide to the binding of a known antigen binding protein to a myostatin polypeptide, several examples of which are disclosed herein.

In another aspect, the present invention provides an antigen binding protein that demonstrates species selectivity. In one embodiment, the antigen binding protein binds to one or more mammalian myostatin, for example, to human myostatin and one or more of mouse, rat, guinea pig, hamster, gerbil, cat, rabbit, dog, goat, sheep, cow, horse, camel, and non-human primate myostatin. In another embodiment, the antigen binding protein binds to one or more primate myostatin, for example, to human myostatin and one or more of cynomolgous, marmoset, rhesus, tamarin and chimpanzee myostatin. In another embodiment, the antigen binding protein binds specifically to human, cynomologous, marmoset, rhesus, tamarin or chimpanzee myostatin. In another embodiment, the antigen binding protein does not bind to one or more of mouse, rat, guinea pig, hamster, gerbil, cat, rabbit, dog, goat, sheep, cow, horse, camel, and non-human primate myostatin. In another embodiment, the antigen binding protein does not bind to a New World monkey species such as a marmoset.

In another embodiment, the antigen binding protein does not exhibit specific binding to any naturally occurring protein other than myostatin. In another embodiment, the antigen binding protein does not exhibit specific binding to any naturally occurring protein other than mammalian myostatin. In another embodiment, the antigen binding protein does not exhibit specific binding to any naturally occurring protein other than primate myostatin. In another embodiment, the antigen binding protein does not exhibit specific binding to any naturally occurring protein other than human myostatin. In another embodiment, the antigen binding protein specifically binds to myostatin from at least one non-human primate, for example, cynomologous monkey, and human myostatin. In another embodiment, the antigen binding protein specifically binds to non-human primate, cynomologous monkey, and human myostatin with a similar binding affinity. In another embodiment, the antigen binding protein blocks an activity of non-human primate, cynomologous monkey, and human myostatin. In another embodiment, the antigen binding protein has a similar $IC_{50}$ or $EC_{50}$ against non-human primate, cynomologous monkey, and human myostatin in an assay as described herein.

One may determine the selectivity of an antigen binding protein for a myostatin using methods well known in the art and following the teachings of the specification. For example, one may determine the selectivity using Western blot, FACS, ELISA, RIA, or by any suitable method that allows determination of binding constants, for example, Biacore® (which utilizes surface plasmon resonance) or KinexA®, a kinetic exclusion assay (see, for example, Ohmura et al., *Anal. Chem.* 73: 3392-3399, 2001).

In another aspect, the present invention provides a myostatin binding antigen binding protein (for example, an anti-myostatin antibody), that has one or more of the following characteristics: binds to both human and non-human primate myostatin, inhibits binding of myostatin to a myostatin receptor, inhibits binding of myostatin to ALK4, co-binds with myostatin/ActRIIB, co-binds with myostatin/ActRIIA, inhibits the ability of myostatin to negatively regulate muscle mass.

Antigen-binding fragments of antigen binding proteins of the invention may be produced by conventional techniques. Examples of such fragments include, but are not limited to, Fab and F(ab')$_2$ fragments. Antibody fragments and derivatives produced by genetic engineering techniques also are contemplated.

Additional embodiments include chimeric antibodies, e.g., humanized versions of non-human (e.g., murine) monoclonal antibodies. Such humanized antibodies may be prepared by known techniques, and offer the advantage of reduced immunogenicity when the antibodies are administered to humans. In one embodiment, a humanized monoclonal antibody comprises the variable domain of a murine antibody (or all or part of the antigen binding site thereof) and a constant domain derived from a human antibody. Alternatively, a humanized antibody fragment may comprise the antigen binding site of a murine monoclonal antibody and a variable domain fragment (lacking the antigen-binding site) derived from a human antibody. Procedures for the production of chimeric and further engineered monoclonal antibodies include those described in Riechmann et al., 1988, Nature 332:323, Liu et al., 1987, Proc. Nat. Acad. Sci. USA 84:3439, Larrick et al., 1989, Bio/Technology 7:934, and Winter et al., 1993, TIPS 14:139. In one embodiment, the chimeric antibody is a CDR grafted antibody. Techniques for humanizing antibodies are discussed in, e.g., U.S. patent application Ser. No. 10/194,975 (published Feb. 27, 2003), U.S. Pat. Nos. 5,869,619, 5,225,539, 5,821,337, 5,859,205, Padlan et al., 1995, FASEB J. 9:133-39, and Tamura et al., 2000, J. Immunol. 164:1432-41.

Procedures have been developed for generating human or partially human antibodies in non-human animals. For example, mice in which one or more endogenous immunoglobulin genes have been inactivated by various means have been prepared. Human immunoglobulin genes have been introduced into the mice to replace the inactivated mouse genes. Antibodies produced in the animal incorporate human immunoglobulin polypeptide chains encoded by the human genetic material introduced into the animal. In one embodiment, a non-human animal, such as a transgenic mouse, is immunized with a myostatin polypeptide, such that antibodies directed against the myostatin polypeptide are generated in the animal. One example of a suitable immunogen is a soluble human myostatin, such as a polypeptide comprising the proteolytic cleavage site of myostatin, or other immunogenic fragment myostatin. Another example of a suitable immunogen is cells expressing high levels of myostatin, or cell membrane preparations therefrom.

Examples of techniques for production and use of transgenic animals for the production of human or partially human antibodies are described in U.S. Pat. Nos. 5,814,318, 5,569,825, and 5,545,806, Davis et al., 2003, *Production of human antibodies from transgenic mice* in Lo, ed. Antibody Engineering: Methods and Protocols, Humana Press, NJ:191-200, Kellermann et al., 2002, Curr Opin Biotechnol. 13:593-97, Russel et al., 2000, Infect Immun. 68:1820-26, Gallo et al., 2000, Eur J. Immun. 30:534-40, Davis et al., 1999, Cancer Metastasis Rev. 18:421-25, Green, 1999, J Immunol Methods. 231:11-23, Jakobovits, 1998, Adv Drug Deliv Rev 31:33-42, Green et al., 1998, J Exp Med. 188:483-95, Jakobovits A, 1998, Exp. Opin. Invest. Drugs. 7:607-14, Tsuda et al., 1997, Genomics 42:413-21, Mendez et al., 1997, Nat. Genet. 15:146-56, Jakobovits, 1994, Curr Biol. 4:761-63, Arbones et al., 1994, Immunity. 1:247-60, Green et al., 1994, Nat. Genet. 7:13-21, Jakobovits et al., 1993, Nature 362:255-58, Jakobovits et al., 1993, Proc Natl Acad Sci USA. 90:2551-55. Chen, J. et al., 1993, Int Immunol 5: 647-656, Choi et al., 1993, Nature Genetics 4: 117-23, Fishwild et al., 1996, Nat Biotechnol 14: 845-51, Harding et al., 1995, Ann NY Acad Sci, Lonberg et al., 1994, Nature 368: 856-59, Lonberg, 1994, Transgenic Approaches to Human Monoclonal Antibodies in Handbook of Experimental Pharmacology 113: 49-101, Lonberg et al., 1995, Int Rev Immunol 13: 65-93, Neuberger, 1996, Nat Biotechnol 14: 826, Taylor et al., 1992, Nucleic Acids Research 20: 6287-95, Taylor et al., 1994, Int Immunol 6: 579-91, Tomizuka et al., 1997, Nat Gen 16: 133-43, Tomizuka et al., 2000, Proc Natl Acad Sci USA. 97: 722-27, Tuaillon et al., 1993, Proc Natl Acad Sci USA. 90: 3720-24, and Tuaillon et al., 1994, J Immunol 152: 2912-20. These and other examples are also discussed in U.S. Patent application publication 2007-0098715, published May 3, 2007.

In another aspect, the present invention provides monoclonal antibodies that bind to myostatin. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibodyproducing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In one embodiment, a hybridoma cell line is produced by immunizing an animal (e.g., a transgenic animal having human immunoglobulin sequences) with a myostatin immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds a myostatin polypeptide. Such hybridoma cell lines, and anti-myostatin monoclonal antibodies produced by them, are encompassed by the present invention.

Monoclonal antibodies secreted by a hybridoma cell line can be purified using any technique known in the art. Hybridomas or mAbs may be further screened to identify mAbs with particular properties, such as the ability to block a myostatin induced activity. Examples of such screens are provided in the examples below.

Monoclonal antibodies can also be produced using a process referred to as genetic immunization. For example, a nucleic acid encoding the antigen of interest can be incorporated into a viral vector (such as an adenoviral vector). The resulting vector is then used to develop an immune response against the antigen of interest in a suitable host animal (for example, a non-obese diabetic, or NOD, mouse). This techniques is substantially described by Ritter et al., Biodrugsl6 (1): 3-10 (2002), the disclosure of which is incorporated by reference herein.

Molecular evolution of the complementarity determining regions (CDRs) in the center of the antibody binding site also has been used to isolate antibodies with increased affinity, for example, antibodies having increased affinity for c-erbB-2, as described by Schier et al., 1996, J. Mol. Biol. 263:551. Accordingly, such techniques are useful in preparing antibodies to myostatin.

Antigen binding proteins directed against a myostatin can be used, for example, in assays to detect the presence of myostatin polypeptides or cells expressing myostatin, either in vitro or in vivo. The antigen binding proteins also may be employed in purifying myostatin proteins by immunoaffinity chromatography. Those antigen binding proteins that additionally can block the interaction of myostatin and a myostatin receptor (or subunit thereof) may be used to inhibit a biological activity that results from such interaction. Blocking antigen binding proteins can be used in the methods of the present invention. Such antigen binding proteins that function as myostatin antagonists may be employed in treating any myostatin-induced condition, including but not limited to sarcopenia, cachexia and muscle-wasting conditions. In one embodiment, a human anti-myostatin monoclonal antibody generated by procedures involving immunization of transgenic mice is employed in treating such conditions. In another embodiment, a humanized anti-myostatin monoclonal antibody is employed in treating such conditions.

Antigen binding proteins may be employed in an in vitro procedure, or administered in vivo to inhibit a myostatin-induced biological activity. Disorders caused or exacerbated (directly or indirectly) by myostatin, examples of which are provided herein, thus may be treated. In one embodiment, the present invention provides a therapeutic method comprising in vivo administration of a myostatin blocking antigen binding protein to a mammal in need thereof in an amount effective for reducing a myostatin-induced biological activity.

Antigen binding proteins of the invention include partially human and fully human monoclonal antibodies that inhibit a biological activity of myostatin. One embodiment is directed to a monoclonal antibody that at least partially blocks the interaction of human myostatin with a myostatin receptor (or subunit thereof). In one embodiment, the antibodies are generated by immunizing a transgenic mouse with a myostatin immunogen. In another embodiment, the immunogen is a human myostatin polypeptide (e.g., a cell transformed or transfected to express myostatin, or a cell that naturally expresses myostatin). Hybridoma cell lines derived from such immunized mice, wherein the hybridoma secretes a monoclonal antibody that binds myostatin, also are provided herein.

Although human, partially human, or humanized antibodies will be suitable for many applications, particularly those involving administration of the antibody to a human subject, other types of antigen binding proteins will be suitable for certain applications. The non-human antibodies of the invention can be, for example, derived from any antibody-producing animal, such as mouse, rat, rabbit, goat, donkey, or non-human primate (such as monkey (e.g., cynomologous or rhesus monkey) or ape (e.g., chimpanzee)). Non-human antibodies of the invention can be used, for example, in in vitro and cell-culture based applications, or any other application where an immune response to the antibody of the invention does not occur, is insignificant, can be prevented, is not a concern, or is desired. In one embodiment, a non-human antibody of the invention is administered to a non-human subject. In another embodiment, the non-human antibody does not elicit an immune response in the non-human subject. In another embodiment, the non-human antibody is from the same species as the non-human subject, e.g., a mouse antibody of the invention is administered to a mouse. An antibody from a particular species can be made by, for example, immunizing an animal of that species with the desired immunogen (e.g., cells expressing myostatin, or a soluble myostatin polypeptide) or using an artificial system for generating antibodies of that species (e.g., a bacterial or phage display-based system for generating antibodies of a particular species), or by converting an antibody from one species into an antibody from another species by replacing, e.g., the constant region of the antibody with a constant region from the other species, or by replacing one or more amino acid residues of the antibody so that it more closely resembles the sequence of an antibody from the other species. In one embodiment, the antibody is a chimeric antibody comprising amino acid sequences derived from antibodies from two or more different species.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, EMBO J. 10: 2821. Appropriate cloning and expression vectors for use with bacterial, fungal, yeast, and mammalian cellular hosts are described by Pouwels et al. (*Cloning Vectors: A Laboratory Manual*, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion of myostatin bound thereto. Polypeptides contemplated for use herein include substantially homogeneous recombinant mammalian anti-myostatin antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-myostatin antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

In one aspect, the present invention provides antigen-binding fragments of an anti-myostatin antibody of the invention. Such fragments can consist entirely of antibody-derived sequences or can comprise additional sequences. Examples of antigen-binding fragments include Fab, F(ab')2, single chain antibodies, diabodies, triabodies, tetrabodies, and domain antibodies. Other examples are provided in Lunde et al., 2002, Biochem. Soc. Trans. 30:500-06.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol. Biol. 178:379-87.

Antigen binding proteins (e.g., antibodies, antibody fragments, and antibody derivatives) of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutein of a naturally occurring constant region.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lantto et al., 2002, *Methods Mol. Biol.* 178: 303-16. Moreover, if an IgG4 is desired, it may also be desired to introduce a point mutation (CPSCP (SEQ ID NO: 52)->CPPCP (SEQ ID NO: 53)) in the hinge region as described in Bloom et al., 1997, *Protein Science* 6:407, incorporated by reference herein) to alleviate a tendency to form intra-H chain disulfide bonds that can lead to heterogeneity in the IgG4 antibodies.

Moreover, techniques for deriving antigen binding proteins having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., 1992, BioTechnology, 10:779.

In another embodiment, the present invention provides an antigen binding protein that has a low dissociation constant from myostatin. In one embodiment, the antigen binding protein has a $K_d$ of 200 pM, or a $K_d$ of 100 pM or lower. In another embodiment, the $K_d$ is 10 pM or lower; in another embodiment, it is 5 pM or lower, or it is 4 pM, 3 pM or 2 pM or lower. In another embodiment, the $K_d$ is substantially the same as an antibody described herein in the Examples. In another embodiment, the antigen binding protein binds to myostatin with substantially the same $K_d$ as an antibody described herein in the Examples.

In another embodiment, the present invention provides an antigen binding protein that has a dissociation constant ($K_d$) for myostatin that is substantially lower than its dissociation constant for GDF-11. In another embodiment, the dissociation constant for myostatin is 1.000-fold lower than that for GDF-11, or it is 2,500, 5,000, 7,500, 8,000, 9,000, 9,500, 9,700, 9,800, 9,900 or 10,000-fold lower for myostatin than GDF-11. In another embodiment, the selectivity of binding to myostatin over GDF-11 is 1,000, 2,500, 5,000, 7,500, 8,000, 9,000, 9,500, 9,700, 9,800, 9,900 or 10,000-fold. In another embodiment, the $K_d$ for GDF-11 is 10 nM or higher; in another embodiment, it is 25 nM or higher, or it is 50 nM, 100 nM, 150 nM, 175 nM or 180 nM or higher. In another embodiment, the selectively of binding to myostatin over GDF-11 is 1,000, 2,500, 5,000, 7,500, 8,000, 9,000, 9,500, 9,700, 9,800, 9,900 or 10,000-fold.

In another embodiment, the present invention provides an antigen binding protein that has a binding affinity for myostatin that is substantially higher than its binding affinity for GDF-11. In one embodiment, the affinity of the antigen binding protein for myostatin is 500-fold higher than for GDF-11. In another embodiment, the affinity for myostatin is 1,000-fold greater than that for GDF-11, or it is 2,500, 5,000, 7,500, 8,000, 9,000, 9,500, 9,700, 9,800, 9,900 or 10,000-fold higher for myostatin than GDF-11.

In another aspect, the present invention provides an antigen binding protein that inhibits an activity of myostatin, for example binding to a myostatin receptor (or subunit thereof), binding to cells expressing a myostatin receptor, or binding of myostatin to ALK4. In one embodiment, the antigen binding protein has an $IC_{50}$ of 1000 pM or lower. In another embodiment, the $IC_{50}$ is 500 pM or lower; in another embodiment, the $IC_{50}$ is 300 pM or lower, or it is 200 pM or lower, or it is 100 pM or lower. In another embodiment, the $IC_{50}$ is substantially the same as that of an antibody described herein in the Examples. In another embodiment, the antigen binding protein inhibits an activity of myostatin with substantially the same $IC_{50}$ as an antibody described herein in the Examples.

In one embodiment, antigen binding proteins of the present invention have an apparent affinity for myostatin (or cells expressing myostatin) of 1000 pM or lower. In other embodiments, the antigen binding proteins exhibit an apparent affinity of 500 pM or lower, 300 pM or lower, 200 pM or lower, 100 pM or lower, or 80 pM or lower. In another embodiment, the antigen binding protein exhibits an apparent affinity substantially the same as that of an antibody described herein in the Examples. In another embodiment, the antigen binding protein has an apparent affinity substantially the same that of an antibody described herein in the Examples.

In another embodiment, the present invention provides an antigen binding protein that competes for binding to myostatin with an antibody disclosed herein. Such competitive ability can be determined by methods that are well-known in the art, for example by competition in binding to myostatin-expressing cells as observed using fluorescence activate cells sorting (FACS) techniques or other, similar assays, by competition in an assay such as a BIACore® or KinExA® assay, or by competition in another assay described herein. In one aspect, an antigen binding protein that competes for binding to myostatin with an antibody disclosed herein binds the same epitope or an overlapping (or adjacent) epitope as the antibody. In another aspect, the antigen binding protein that competes for binding to myostatin with an antibody disclosed herein inhibits an activity of myostatin.

In another aspect, the present invention provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO 00/09560, published Feb. 24, 2000, incorporated by reference.

The present invention further provides multi-specific antigen binding proteins, for example, bispecific antigen binding protein, e.g., antigen binding protein that bind to two different epitopes of myostatin, or to an epitope of myostatin and an epitope of another molecule, via two different antigen binding sites or regions. Moreover, bispecific antigen binding protein as disclosed herein can comprise a myostatin binding site from one of the herein-described antibodies and a second myostatin binding region from another of the herein-described antibodies, including those described herein by reference to other publications. Alternatively, a bispecific antigen binding protein may comprise an antigen binding site from one of the herein described antibodies and a second antigen binding site from another myostatin antibody that is known in the art, or from an antibody that is prepared by known methods or the methods described herein.

Numerous methods of preparing bispecific antibodies are known in the art, and discussed in U.S. patent application Ser. No. 09/839,632, filed Apr. 20, 2001 (incorporated by reference herein). Such methods include the use of hybrid-hybridomas as described by Milstein et al., 1983, Nature 305:537, and others (U.S. Pat. No. 4,474,893, U.S. Pat. No. 6,106,833), and chemical coupling of antibody fragments (Brennan et al., 1985, Science 229:81; Glennie et al., 1987, J. Immunol. 139: 2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, J. Immnol. 148:1547) or other lock and key interactive domain structures as described in U.S. Pat. No. 5,582, 996. Additional useful techniques include those described in Kortt et al., 1997, supra; U.S. Pat. No. 5,959,083; and U.S. Pat. No. 5,807,706.

In another aspect, the antigen binding protein of the present invention comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin)), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols. US Pat. App. No. 20030195154.

A further aspect of the present invention includes variants of the antibodies described herein. Certain variants are encompassed by consensus sequences set forth herein, for example, in SEQ ID NOs:10 and 20. Additional variants include antibodies which differ from the antibodies disclosed herein by one or more amino acid(s), for example, one, two three, four, five, six, seven, eight, nine or ten amino acids of a variant antibody differ from those of the disclosed antibody sequences. In another embodiment, a variant is 90% identical in amino acid sequence to one of the disclosed antibodies. In another embodiment, a variant antibody sequence is 91%, 92%, 93%, 94%, 95%, 96%, 97%, 98%, or 99% identical to that of one of the antibodies disclosed herein. Variants also include antibody sequences from which one or more amino acids have been deleted, for example, one, two, three, four or five amino acids may be deleted from either terminus of an antibody polypeptide, or such deletions may be made internally. Additional embodiments are encompassed by the term "variants." For example, amino acid residues may undergo post-translational modifications, including but not limited to, glutamine (in particular, glutamine at the N-terminus) may be cyclized or converted to pyroglutamic acid; additionally or alternatively, amino acids may undergo deamidation, isomerization, glycation and/or oxidation. The polypeptides of the invention may undergo additional post-translational modification, including glycosylation, for example N-linked or O-linked glycosylation, at sites that are well-known in the art. Accordingly, changes may be made in the amino acid sequence of a polypeptide to preclude or minimize such alterations, or to facilitate them in circumstances where such processing is beneficial.

In another aspect, the present invention provides methods of screening for a molecule that binds to myostatin using the antigen binding proteins of the present invention. Any suitable screening technique can be used. In one embodiment, a myostatin molecule, or a fragment thereof to which an antigen binding protein of the present invention binds, is contacted with the antigen binding protein of the invention and with another molecule, wherein the other molecule binds to myostatin if it reduces the binding of the antigen binding protein to myostatin. Binding of the antigen binding protein can be detected using any suitable method, e.g., an ELISA. Detection of binding of the antigen binding protein to myostatin can be simplified by detectably labeling the antigen binding protein, as discussed above. In another embodiment, the myostatin-binding molecule is further analyzed to determine whether it inhibits myostatin activation and/or signaling.

Also comprehended by the invention are pharmaceutical compositions comprising effective amounts of polypeptide products of the invention together with pharmaceutically acceptable diluents, preservatives, solubilizers, emulsifiers, adjuvants and/or carriers useful in myostatin therapy. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); covalent attachment of moieties, such as polymers (for example, polyethylene glycol or other moieties) to the protein (as discussed supra, see also, for example U.S. Pat. No. 4,179,337 hereby incorporated by reference); incorporation of the material into particulate preparations of polymeric compounds such as polylactic acid, polyglycolic acid, etc. or into liposomes. Such compositions will influence the physical state, stability, rate of in vivo release, and rate of in vivo clearance of myostatin. See, e.g., Remington's Pharmaceutical Sciences, 18th Ed. (1990, Mack Publishing Co., Easton, Pa. 18042) pages 1435-1712 which are herein incorporated by reference.

Generally, an effective amount of the present myostatin-inhibitory polypeptides will be determined by the age, weight and condition or severity of disease of the recipient. See, Remingtons Pharmaceutical Sciences, supra, at pages 697-773, herein incorporated by reference. Typically, a dosage of between about 0.001 g/kg body weight to about 1 g/kg body weight, may be used, but more or less, as a skilled practitioner will recognize, may be used. For local (i.e., non-systemic) applications, such as topical applications, the dosing may be between about 0.001 $g/cm^2$ to about 1 $g/cm^2$. Dosing may be one or more times daily, or less frequently, and may be in conjunction with other compositions as described herein. It should be noted that the present invention is not limited to the dosages recited herein.

The present invention provides pharmaceutical compositions and methods of treating various disorders using myostatin antagonists including myostatin binding agents (or myostatin binding polypeptides, including antibodies). The invention provides a method of treating the effects of hypogonadism in a subject in need thereof comprising administering a therapeutically effective amount of at least one myostatin antagonist to the subject in admixture with a pharmaceutically acceptable carrier. In one embodiment the hypogonadism results from androgen deprivation therapy. In a second embodiment, the hypogonadism results from age-related decrease in gonadal functioning.

The present invention also provides a method of treating cachexia in a subject suffering from such a condition comprising administering a therapeutically effective amount of at least one myostatin antagonist to the subject in admixture with a pharmaceutically acceptable carrier. The condition may be primary cachexia, or secondary cachexia. In one embodiment, the subject is afflicted with rheumatoid cachexia, or cachexia that occurs as a result or complication of another autoimmune or inflammatory condition (including chronic obstructive pulmonary disease, or COPD). The present invention also provides a method of treating cachexia due to burn injuries in a subject in need thereof comprising administering a therapeutically effective amount of at least one myostatin antagonist to the subject in admixture with a pharmaceutically acceptable carrier. The present invention also provides a method of reducing tumor necrosis factor (TNF)-alpha in a subject suffering from an inflammatory condition characterized by excessive TNF-alpha.

The present invention also provides a method of treating cachexia due to treatment with chemical agents such as chemotherapeutic agents to a subject in need to such a treatment comprising administering a therapeutically effective amount of at least one myostatin antagonist in admixture with a pharmaceutically acceptable carrier to the subject. The present invention also provides a method of treating cachexia in an individual afflicted with cancer or a neoplastic condition, when the cachexia is due to the cancer or neoplastic condition, to any treatment for the cancer or a neoplastic condition, or is a combined effect of the condition and the treatment.

The present invention also provides a method of treating cachexia due to diabetes to a subject in need of such a treatment comprising administering a therapeutically effective amount of at least one myostatin antagonist in admixture with a pharmaceutically acceptable carrier to the subject. The present invention also provides a method of treating diabetic nephropathy in a subject suffering from such a condition comprising administering a therapeutically effective amount of at least one myostatin antagonist in admixture with a pharmaceutically acceptable carrier to the subject.

Also provided by the present invention are methods of treating cardiac cachexia, and/or renal cachexia, comprising administering a therapeutically effective amount of at least one myostatin antagonist in admixture with a pharmaceutically acceptable carrier to the subject. Cachexia is a common complication of chronic heart failure (CHF), in which it is linked to increased plasma levels of inflammatory cytokines, such as TNF-alpha, and an imbalance of catabolic/anabolic pathways. Subjects afflicted with chronic renal failure (CRF)

and/or end-stage renal disease (ESRD) are also often afflicted with cachexia, which may also be attributed to elevated levels of pro-inflammatory agents.

Further provided herein are methods of treating cardiac atrophy, and/or cardiac hypotrophy. Cardiac atrophy can occur in individuals afflicted with cancer, and also in individuals on prolonged bed-rest, or under other situations or conditions that result in voluntary muscle atrophy. Additionally, the present selective myostatin antagonists may also be used to treat other conditions in which the heart muscle is reduced in effectiveness, for example, heart failure (for example, congestive heart failure). The present invention may also be useful treating cardiac abnormalities that occur in eating disorders or starvation.

The present invention also provides an alternative method of treating diseases or conditions formerly treated by growth hormone, insulin growth factor-1 (IGF-1), growth hormone secretagogues, and other agents related to the growth hormone-IGF-1 axis. Myostatin antagonists provide a method of treating such diseases without the potentially dangerous side-effects of these agents. Myostatin antagonists also provide a method for treating growth hormone resistance (a recognized problem in aging). In one embodiment, the present invention provides a method of treating the effects of Prader-Willi syndrome in a subject suffering from such a condition comprising administering a therapeutically effective amount of at least one myostatin antagonist to the subject in admixture with a pharmaceutically acceptable carrier.

The present invention also provides a method of treating sarcopenia, including sarcopenia of the elderly, and other muscle disease or conditions, comprising administering a therapeutically effective amount of at least one myostatin antagonist in admixture with a pharmaceutically acceptable carrier to the subject. The present invention further provides a method of treating frailty of the elderly, including use in rehabilitative therapy, and in conjunction with strength and/or balance training, as well as in the reduction or prevention of falls.

Also provided by the present invention are methods of facilitating the healing of traumatic bone fracture, and repair of osteoporotic fracture, as well as treatment of bone loss in general (for example, osteoporosis and/or osteopenia) and as a result of concomitant prolonged inactivity or bed-rest, and/or immobilization of limbs.

Other conditions for which administration of a myostatin antagonist would prove beneficial include Addison's disease, amyotrophic lateral sclerosis or motor neuron disease (ALS; MND; Lou Gehrig's disease), Bell's palsy (and/or facial nerve problems), botulism, cerebral palsy, Charcot-Marie-Tooth disease and other peripheral neuropathies, Cushing's syndrome, diabetic neuropathy, Guillan-Barre syndrome, multiple sclerosis, muscular atrophy (including progressive and spinal muscular atrophy), muscular dystrophy (of which there are numerous forms; including myotonic dystrophy), myasthenia gravis, poliomyelitis, polymyositis, sprains and strains of muscles, tendons and/or ligaments, stroke, and other conditions that result in muscle wasting, such as prolonged inactivity or bed-rest, immobilization of limbs (for example, by casting and/or splinting), and space flight.

The myostatin binding proteins of the present invention may also find uses in diagnostic methods. For example, antigen binding proteins of the invention may be "labeled" by association with a detectable marker substance (e.g., radiolabeled with $^{125}$I or conjugated to another detectable moiety) to provide reagents useful in detection and quantification of myostatin in solid tissue and fluid samples such as blood or urine. Contemplated herein are kits containing such labeled materials.

The following examples are provided for the purpose of illustrating specific embodiments or features of the instant invention and do not limit its scope.

EXAMPLE 1

Anti-Myostatin Antibodies

Several variant anti-myostatin antibodies were prepared, and tested for activity; their sequences are shown in Tables 1 and 2 below.

TABLE 1

Anti-Myostatin Antibody Heavy Chain Sequences

| COMPLETE HEAVY CHAIN (HC) SEQ ID NO: | ANTI-MYOSTATIN ANTIBODY |
|---|---|
| 11 | 12A5-1 |
| 12 | 12A5-3 |
| 13 | 12A5-5 |
| 14 | 12A5-6 |
| 15 | 12A5-8 |
| 16 | 12A5-9 |
| 17 | 12A5-10 |
| 18 | 12A5-12 |
| 19 | 12A5-18 |
| 20 | CONSENSUS |

| ANTI-MYOSTATIN ANTIBODY | HC FR1 | HC CDR1 | HC FR2 |
|---|---|---|---|
| 12A5-1 | EVQLVESGGGLVQPGGSLRLSCAASGFTFS (SEQ ID NO: 26) | NYWMN (SEQ ID NO: 28) | WVRQAPGKGLEWVA (SEQ ID NO: 32) |
| 12A5-3 | EVQLVESGGGLVQPGGSLRLSCAASGFTFS (SEQ ID NO: 26) | NYWCN (SEQ ID NO: 29) | WVRQAPGKGLEWVA (SEQ ID NO: 32) |
| 12A5-5 | EVQLVESGGGLVQPGGSLRLSCAASGFTFS (SEQ ID NO: 26) | RYWMN (SEQ ID NO: 30) | WVRQAPGKGLEWVA (SEQ ID NO: 32) |

TABLE 1-continued

Anti-Myostatin Antibody Heavy Chain Sequences

| | | | |
|---|---|---|---|
| 12A5-6 | EVQLVESGGGLVQPGGSLRLSCAASGFTFS (SEQ ID NO: 26) | RYWMN (SEQ ID NO: 30) | WVRQAPGKGLEWVA (SEQ ID NO: 32) |
| 12A5-8 | EVQLVESGGGLVQPGGSLRLSCAASGFTFR (SEQ ID NO: 27) | NYWCN (SEQ ID NO: 29) | WVRQAPGKGLEWVA (SEQ ID NO: 32) |
| 12A5-9 | EVQLVESGGGLVQPGGSLRLSCAASGFTFR (SEQ ID NO: 27) | NYWCN (SEQ ID NO: 29) | WVRQAPGKGLEWVA (SEQ ID NO: 32) |
| 12A5-10 | EVQLVESGGGLVQPGGSLRLSCAASGFTFR (SEQ ID NO: 27) | NYWCN (SEQ ID NO: 29) | WVRQAPGKGLEWVA (SEQ ID NO: 32) |
| 12A5-12 | EVQLVESGGGLVQPGGSLRLSCAASGFTFS (SEQ ID NO: 27) | NYWLN (SEQ ID NO: 31) | WVRQAPGKGLEWVA (SEQ ID NO: 32) |
| 12A5-18 | EVQLVESGGGLVQPGGSLRLSCAASGFTFR (SEQ ID NO: 27) | NYWCN (SEQ ID NO: 29) | WVRQAPGKGLEWVA (SEQ ID NO: 32) |

| ANTI-MYOSTATIN ANTIBODY | HC CDR2 | HC FR3 |
|---|---|---|
| 12A5-1 | QIRLKSDNYATHYAESVKG (SEQ ID NO: 33) | RFTISRDNAKNSLYLQMNSLRAEDTAVYYCAR (SEQ ID NO: 34) |
| 12A5-3 | QIRLKSDNYATHYAESVKG (SEQ ID NO: 33) | RFTISRDNAKNSLYLQMNSLRAEDTAVYYCTE (SEQ ID NO: 35) |
| 12A5-5 | QIRLKSDNYATHYAESVKG (SEQ ID NO: 33) | RFTISRDNAKNSLYLQMNSLRAEDTAVYYCTE (SEQ ID NO: 35) |
| 12A5-6 | QIRLKSDNYATHYAESVKG (SEQ ID NO: 33) | RFTISRDNAKNSLYLQMNSLRAEDTAVYYCTE (SEQ ID NO: 35) |
| 12A5-8 | QIRLKSDNYATHYAESVKG (SEQ ID NO: 33) | RFTISRDNAKNSLYLQMNSLRAEDTAVYYCTE (SEQ ID NO: 35) |
| 12A5-9 | QIRLKSDNYATHYAESVKG (SEQ ID NO: 33) | RFTISRDNAKNSLYLQMNSLRAEDTAVYYCTE (SEQ ID NO: 35) |
| 12A5-10 | QIRLKSDNYATHYAESVKG (SEQ ID NO: 33) | RFTISRDNAKNSLYLQMNSLRAEDTAVYYCTE (SEQ ID NO: 35) |
| 12A5-12 | QIRLKSDNYATHYAESVKG (SEQ ID NO: 33) | RFTISRDNAKNSLYLQMNSLRAEDTAVYYCTE (SEQ ID NO: 35) |
| 12A5-18 | QIRLKSDNYATHYAESVKG (SEQ ID NO: 33) | RFTISRDNAKNSLYLQMNSLRAEDTAVYYCTE (SEQ ID NO: 35) |

| ANTI-MYOSTATIN ANTIBODY | HC CDR3 | HC FR4 |
|---|---|---|
| 12A5-1 | GLDY (SEQ ID NO: 36) | WGQGTTVTVSS (SEQ ID NO: 37) |
| 12A5-3 | GLDY (SEQ ID NO: 36) | WGQGTTVTVSS (SEQ ID NO: 37) |
| 12A5-5 | GLDY (SEQ ID NO: 36) | WGQGTTVTVSS (SEQ ID NO: 37) |
| 12A5-6 | GLDY (SEQ ID NO: 36) | WGQGTTVTVSS (SEQ ID NO: 37) |
| 12A5-8 | GLDY (SEQ ID NO: 36) | WGQGTTVTVSS (SEQ ID NO: 37) |
| 12A5-9 | GLDY (SEQ ID NO: 36) | WGQGTTVTVSS (SEQ ID NO: 37) |
| 12A5-10 | GLDY (SEQ ID NO: 36) | WGQGTTVTVSS (SEQ ID NO: 37) |
| 12A5-12 | GLDY (SEQ ID NO: 36) | WGQGTTVTVSS (SEQ ID NO: 37) |
| 12A5-18 | GLDY (SEQ ID NO: 36) | WGQGTTVTVSS (SEQ ID NO: 37) |

TABLE 2

Anti-Myostatin Antibody Light Chain Sequences

| COMPLETE LIGHT CHAIN (LC) SEQ ID NO: | ANTI-MYOSTATIN ANTIBODY |
|---|---|
| 1 | 12A5-1 |
| 2 | 12A5-3 |

TABLE 2-continued

Anti-Myostatin Antibody Light Chain Sequences

| 3 | 12A5-5 |
| 4 | 12A5-6 |
| 5 | 12A5-8 |
| 6 | 12A5-9 |
| 7 | 12A5-10 |
| 8 | 12A5-12 |
| 9 | 12A5-18 |
| 10 | CONSENSUS |

| ANTI-MYOSTATIN ANTIBODY | LC FR1 | LC CDR1 | LC FR2 | LC CDR2 |
|---|---|---|---|---|
| 12A5-1 | DIQMTQSPSSLSASVGDRVTITC (SEQ ID NO: 38) | KASQDINKYVA (SEQ ID NO: 39) | WYQQKPGKAPKLLIY (SEQ ID NO: 40) | YTSTLQP (SEQ ID NO: 41) |
| 12A5-3 | DIQMTQSPSSLSASVGDRVTITC (SEQ ID NO: 38) | KASQDINKYVA (SEQ ID NO: 39) | WYQQKPGKAPKLLIY (SEQ ID NO: 40) | YTSFLQP (SEQ ID NO: 42) |
| 12A5-5 | DIQMTQSPSSLSASVGDRVTITC (SEQ ID NO: 38) | KASQDINKYVA (SEQ ID NO: 39) | WYQQKPGKAPKLLIY (SEQ ID NO: 40) | YTSWLQP (SEQ ID NO: XX43) |
| 12A5-6 | DIQMTQSPSSLSASVGDRVTITC (SEQ ID NO: 38) | KASQDINKYVA (SEQ ID NO: 39) | WYQQKPGKAPKLLIY (SEQ ID NO: 40) | YTSFLQP (SEQ ID NO: 42) |
| 12A5-8 | DIQMTQSPSSLSASVGDRVTITC (SEQ ID NO: 38) | KASQDINKYVA (SEQ ID NO: 39) | WYQQKPGKAPKLLIY (SEQ ID NO: 40) | YTKTLQP (SEQ ID NO: 44) |
| 12A5-9 | DIQMTQSPSSLSASVGDRVTITC (SEQ ID NO: 38) | KASQDINKYVA (SEQ ID NO: 39) | WYQQKPGKAPKLLIY (SEQ ID NO: 40) | YTRTLQP (SEQ ID NO: 45) |
| 12A5-10 | DIQMTQSPSSLSASVGDRVTITC (SEQ ID NO: 38) | KASQDINKYVA (SEQ ID NO: 39) | WYQQKPGKAPKLLIY (SEQ ID NO: 40) | YTSTLQP (SEQ ID NO: 41) |
| 12A5-12 | DIQMTQSPSSLSASVGDRVTITC (SEQ ID NO: 38) | KASQDINKYVA (SEQ ID NO: 39) | WYQQKPGKAPKLLIY (SEQ ID NO: 40) | YTSWLQP (SEQ ID NO: 43) |
| 12A5-18 | DIQMTQSPSSLSASVGDRVTITC (SEQ ID NO: 38) | KASQDINKYVA (SEQ ID NO: 39) | WYQQKPGKAPKLLIY (SEQ ID NO: 40) | YTSHLQP (SEQ ID NO: 46) |

| ANTI-MYOSTATIN ANTIBODY | LC FR3 | LC CDR3 | LC FR4 |
|---|---|---|---|
| 12A5-1 | GVPSRFSGSGSGTDFTFTISSLQPEDIATYYC (SEQ ID NO: 47) | LQYDNLLYT (SEQ ID NO: 48) | FGQGTKLEIK (SEQ ID NO: 51) |
| 12A5-3 | GVPSRFSGSGSGTDFTFTISSLQPEDIATYYC (SEQ ID NO: 47) | LQYDNLLYT (SEQ ID NO: 48) | FGQGTKLEIK (SEQ ID NO: 51) |
| 12A5-5 | GVPSRFSGSGSGTDFTFTISSLQPEDIATYYC (SEQ ID NO: 47) | LQYDNLLYT (SEQ ID NO: 48) | FGQGTKLEIK (SEQ ID NO: 51) |
| 12A5-6 | GVPSRFSGSGSGTDFTFTISSLQPEDIATYYC (SEQ ID NO: 47) | LQYDALLYT (SEQ ID NO: 49) | FGQGTKLEIK (SEQ ID NO: 51) |
| 12A5-8 | GVPSRFSGSGSGTDFTFTISSLQPEDIATYYC (SEQ ID NO: 47) | LQYDNLLYT (SEQ ID NO: 48) | FGQGTKLEIK (SEQ ID NO: 51) |
| 12A5-9 | GVPSRFSGSGSGTDFTFTISSLQPEDIATYYC (SEQ ID NO: 47) | LQYDNLLYT (SEQ ID NO: 48) | FGQGTKLEIK (SEQ ID NO: 51) |
| 12A5-10 | GVPSRFSGSGSGTDFTFTISSLQPEDIATYYC (SEQ ID NO: 47) | LQYDNKLYT (SEQ ID NO: 50) | FGQGTKLEIK (SEQ ID NO: 51) |
| 12A5-12 | GVPSRFSGSGSGTDFTFTISSLQPEDIATYYC (SEQ ID NO: 47) | LQYDNLLYT (SEQ ID NO: 48) | FGQGTKLEIK (SEQ ID NO: 51) |
| 12A5-18 | GVPSRFSGSGSGTDFTFTISSLQPEDIATYYC (SEQ ID NO: 47) | LQYDNLLYT (SEQ ID NO: 48) | FGQGTKLEIK (SEQ ID NO: 51) |

EXAMPLE 2

In Vitro Assays

The activity(ies) of anti-myostatin antibodies are evaluated in several assays.

C2C12 Cell Based Myostatin Activity Assay

This assay demonstrates the myostatin neutralizing capability of the inhibitor being tested by measuring the extent that binding of myostatin to its receptor is inhibited.

A myostatin-responsive reporter cell line was generated by transfection of C2C12 myoblast cells (ATCC No: CRL-1772) with a pMARE-luc construct. The pMARE-luc construct was made by cloning twelve repeats of the CAGA sequence, representing the myostatin/activin response elements (Dennler et al. EMBO 17: 3091-3100 (1998)) into a pLuc-MCS reporter vector (Stratagene cat #219087) upstream of the TATA box. The myoblast C2C12 cells naturally express myostatin/activin receptors on the cell surface. When myostatin binds the cell receptors, the Smad pathway is activated, and phosphorylated Smad binds to the response element (Macias-Silva et al. Cell 87:1215 (1996)), resulting in the expression of the luciferase gene. Luciferase activity is then measured using a commercial luciferase reporter assay kit (cat #E4550, Promega, Madison, Wis.) according to manufacturer's protocol. A stable line of C2C12 cells that had been transfected with pMARE-luc (C2C12/pMARE clone #44) was used to measure myostatin activity according to the following procedure.

Equal numbers of the reporter cells (C2C12/pMARE clone #44) are plated into 96 well cultures. Recombinant mature myostatin is pre-incubated for one hour at room temperature with antibodies to be tested. The reporter cell culture is treated with the myostatin with or without antibodies for six hours. Myostatin activity is measured by determining the luciferase activity in the treated cultures. This assay can be used to initially identify antibodies that inhibit myostatin signaling activity; titration curves can be generated using varied concentrations of antibody with fixed concentration of myostatin. Such titration curves are used to determine $IC_{50}$ values for a number of the antibodies, as shown in Table 3 below.

TABLE 3

$IC_{50}$ of various anti-myostatin antibody variants

| Antibody | $IC_{50}$ (nM) |
|---|---|
| 12A5-1 | 473.0 |
| 12A5-3 | 2.53 |
| 12A5-5 | 1.85 |
| 12A5-6 | 1.64 |
| 12A5-8 | 4.96 |
| 12A5-9 | 3.98 |
| 12A5-10 | 3.08 |
| 12A5-12 | 1.45 |
| 12A5-18 | 1.45 |

Monoclonal antibody 12A5-5 was chosen for further analysis.

Binding of Myostatin in KinExA™ Solution Equilibrium Assay

Solution-based equilibrium-binding assays using KinExA® technology (Sapidyne Instruments, Inc.) are employed to determine the dissociation equilibrium ($K_d$) of myostatin binding to antibody molecules. This solution-based assay is considered to be more sensitive than the BIAcore® assay in some instances. Reacti-Gel 6×(a highly reactive, cross-linked 6% agarose bead for immobilization of amine-containing ligands; Thermo Scientific Pierce, Rockford, Ill.) is pre-coated with about 50 microG/ml myostatin overnight, and then blocked with bovine serum albumin (BSA; 1 mg/ml). Antibody samples (10 pM, and 30 pM) were incubated with various concentrations (0.5 pM to 5 nM) of myostatin in sample buffer containing 0.1 mg.ml BSA at room temperature for eight hours before being run through the myostatin-coated beads. The amount of the bead-bound antibody is quantified by fluorescent (Cy5) labeled goat anti-human-Fc antibody at 1 mg/ml in SuperBlock® (an optimized protein-based solution for blocking excess binding sites; Thermo Scientific Pierce, Rockford, Ill.). The binding signal is proportional to the concentration of free antibody at equilibrium with a given myostatin concentration. $K_d$ is obtained from the nonlinear regression of the competition curves using a dual-curve one-site homogeneous binding model provided in the KinExA™ software (Sapidyne Instruments, Inc.). Antibody 12A5-5 exhibited a $K_d$ of approximately 2 pM in this assay.

Selectivity Assays using Biacore™

Binding specificity analysis was carried out for 12A5-5 using Biacore™, a label-free surface plasmon resonance (SPR) based technology for studying biomolecular interactions in real time (GE Healthcare, Chalfont St. Giles, UK). 12A5-5, and ActRIIB/Fc were made in house, TGFbetaR11/Fc and BMPR-1A/Fc were from R & D Systems (Minneapolis, Minn.). Both Mab 12A5-5 and the receptors were covalently coupled to research grade sensor chips according to manufacturer's suggested protocol. Ten nanomolar of each of the ligands was flowed over immobilized high density antibody and receptor surfaces. Binding of Myostatin, GDF11, GDF3, Activin A, Activin AB, Activin AC, TGF-beta1, BMP4, BMP9, and BMP10 to their corresponding receptors was tested and used as control to normalize the signals of the ligands binding to 12A5-5 and the other receptors. The data clearly indicated that Mab 12A5-5 does not bind to GDF3, Activin A, Activin AB, Activin AC, TGF-beta1, BMP4, BMP9, or BMP10. Antibody 12A5-5 showed weak binding to GDF11 with the affinity ($K_d$) estimated to be 180 nM in a separate experiment. The results indicated that antibody 12A5-5 was specific for myostatin, and exhibited almost 10,000-fold selectivity for myostatin over GDF11.

EXAMPLE 3

Additional In Vitro Assays

Cell-Based Assay Comparing Inhibition of Myostatin Versus Inhibition of GDF-11

Cell-based assays are carried out substantially as described previously, comparing the $IC_{50}$ of the inhibition of binding of myostatin versus that of GDF-11. Results are shown in Table 4 below.

TABLE 4

Inhibition of Myostatin or GDF-11 Activity

| Cell Assay ($IC_{50}$) | 12A5-5 | Control peptide |
|---|---|---|
| Myostatin | 1.2 nM | 1.1 nM |
| GDF-11 | No neutralization | 1.2 nM |

These results indicate that 12A5-5 inhibited the activity of myostatin in this assay, as did a control polypeptide (described in U.S. Pat. No. 7,511,012) however, while the control peptide also inhibited the activity of GDF-11, antibody 12A5-5 did not.

Binding Assay on ALK4, ActRIIA, and ActRIIB/Fc Surface

Myostatin binding assays are carried out using the Biacore™ system with immobilized ALK4/Fc, ActRIIA/Fc, and ActRIIB/Fc (R&D Systems, Minneapolis, Minn.) surfaces, substantially as described previously for myostatin. The binding signal of myostatin to the immobilized receptors was measured in the presence or absence of antibodies in solution, and compared to the binding signal of myostatin in the absence of antibody, which was assigned as 100% (control). A decreased binding response indicated that antibody binding to myostatin blocked the binding of myostatin to the receptor subunit, while an increased binding response indicated co-binding of the antibody to the myostatin/receptor complex. Results are shown in Table 5 below.

TABLE 5

Effect of 12A5-5 on Binding of Myostatin to Myostatin Receptor Subunits

|  | Alk4-Fc | ActRIIA-Fc | ActRIIB-Fc |
|---|---|---|---|
| 10 nM myostatin alone (myo) | 100% | 100% | 100% |
| myo + 20 nM MAb 12A5-5 | 13% | 617% | 807% |
| myo + 20 nM control polypeptide | 11% | 565% | 560% |

These results indicate that 12A5-5 and a control polypeptide (described previously) blocked myostatin/ALK4 interaction, but co-bound with myostatin/ActRIIB and myostatin/ActRIIA.

Binding to Promyostatin in KinExA™ Solution Equilibrium Assay

A KinExA™ assay similar to the one previously described was run, using promyostatin instead of mature myostatin. Reacti-Gel 6× is pre-coated with about 50 microG/ml promyostatin for over-night, and then blocked with BSA. Ten pM of antibody samples were incubated with various concentrations (0.5 pM to 5 nM) of promyostatin in sample buffer at room temperature for 8 hours before being run through the promyostatin-coated beads. The amount of the bead-bound antibody is quantified substantially as previously described. $K_d$ was obtained from the nonlinear regression as described; antibody 12A5-5 bound promyostatin with a $K_d$ of ~2 pM.

EXAMPLE 4

In Vivo Anabolic Activity of Antibodies

The C57BL6 mouse model (Charles River Laboratories, Massachusetts) is used to determine the in vivo efficacy of the myostatin inhibitors of the present invention. This model responded to the inhibitors of the present invention with a rapid anabolic response which was associated with increased dry muscle mass and an increase in myofibrillar proteins but was not associated with accumulation in body water content.

Figure 2:
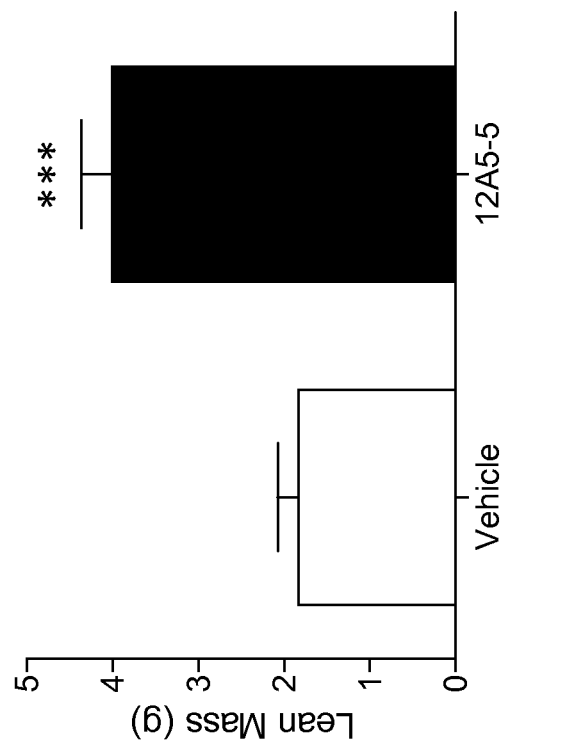
FIG. 2 presents the change in lean body mass on week 4 as determined by nuclear magnetic resonance (NMR).

In one example, the efficacy of 12A5-5 in vivo was demonstrated by the following experiment. A group of eight 8-week old C57BL6 mice were treated once weekly with dosage of 10 mg/kg (subcutaneous injection). The control group of eight 8-week old C57BL6 mice received a weekly (subcutaneous) injection of vehicle (PBS). The animals were weighed every week and lean body mass determined by NMR on week 0 and week 4. The result is shown in FIGS. 1 and 2. FIG. 1 shows the increase in total body weight of the mice over 4 weeks for the administration of antibody compared with the control. In the Figure, anti-myostatin antibody 12A5-5 is represented with solid diamonds and the control with open circles; P values for the various data points are as follows: $*=p<0.05$; $=P<0.01$; and $*=p<0.001$. FIG. 2 shows the change in lean body mass on week 4 as determined by nuclear magnetic resonance (NMR) imaging (EchoMRI 2003, Echo Medical Systems, Houston, Tex.); P values are as described previously.

Accordingly, myostatin antagonist 12A5-5 resulted in increased body weight and an increase in lean muscle mass in mice; similar results were demonstrated in a cynomologous monkey study.

EXAMPLE 5

Identification of Epitope(s) for Anti-Myostatin Neutralizing Monoclonal Antibody 12A5-5

Figure 3:
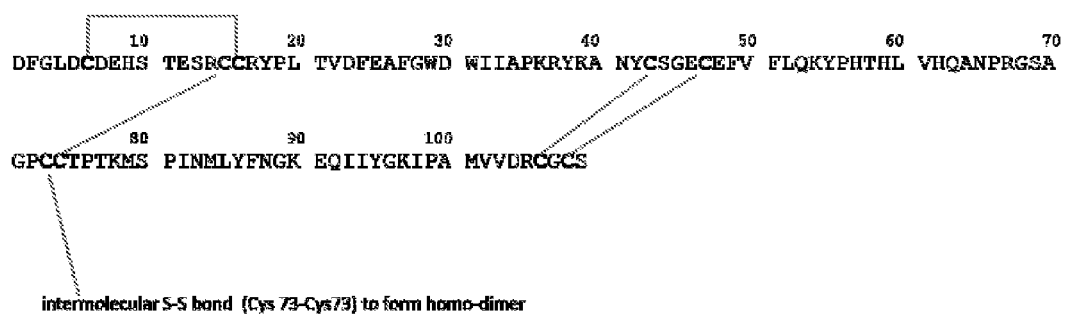
FIG. 3 presents the amino acid sequence (SEQ ID NO: 25) of mature form human myostatin with intramolecular and intermolecular disulfide linkages designated. Disulfide bonds Cys15-Cys74, Cys43-Cys106, and Cys47-Cys108 form a cystine knot structure

The mature form of human myostatin is a 109 amino acid protein with nine cysteines in the molecule that form intramolecular and intermolecular disulfide bonds (shown in FIG. 3). An eight-member ring structure is formed via Cys43-Cys106 and Cys47-Cys108 disulfide bonding. The Cys15-Cys74 disulfide bond penetrates through the ring structure formed by the other disulfide bonds and creates a cystine-knot structure. Cys6 and Cys16 form a disulfide bond at the N-terminal region, which is not part of the cystine-knot. An intermolecular disulfide linkage between Cys73 of a first myostatin monomer and Cys73 of a second myostatin monomer is formed to make native myostatin a covalently linked dimer. The two myostatin monomers are three dimensionally folded as anti-parallel structures in the native state (Cash et al., *EMBO J.* (2009) 28, 2662-2676).

The general approach for characterizing the epitope(s) important for binding of 12A5-5 involved fragmenting human myostatin into peptides with different proteases and/or chemical agents, determining the sequence of the various human myostatin peptides, isolating these peptides, and testing each of them for their ability to bind 12A5-5 using a BIAcore® based competition assay. Further studies using similar proteolytic digestions were performed with human myostatin which had been pre-incubated with 12A5-5, which resulted in protection of proteolytic sites near the binding regions (detected by peptide mapping). Antibody protection on proteolysis of human myostatin results in decreased signals for those peptides that are protected from proteolysis by antibody, and the generation of peptide(s) that bind the antibody after being isolated from HPLC (high-performance liquid chromatography) peptide mapping. The resulting data thus permitted the region(s) important for high-affinity binding of 12A5-5 to myostatin to be determined.

Peptide Isolation and Identification

Peptide digests were subjected to HPLC peptide mapping; the individual peaks were collected; and the peptides identified and mapped by electrospray ionization (ESI) LC-MS/MS (liquid chromatography—mass spectrometry/mass spectrometry) peptide mapping analyses, by matrix assisted laser desorption mass spectrometry (MALDI-MS) and/or by N-terminal sequencing. All HPLC analyses for these studies were performed using a reverse-phase C18 column (0.5 mm i.d.×25 cm length; Zorbax® 300SB; 5 micron; Agilent Technologies, Santa Clara, Calif.). HPLC peptide mapping analyses was developed with multi-step linear gradients from 0.1% trifluoroacetic acid (mobile phase A) to 90% acetonitrile in 0.1 trifluoroacetic acid (mobile phase B). Columns were equilibrated at 98% mobile phase A/2% mobile phase B and developed over 100 minutes of a programmed gradient elution at a flow rate of 15 microliter/min described in the following: isocratic elution at 2% mobile phase B for 5 min followed by two linear gradient elutions from 2% to 50% mobile phase B for 90 min and from 50% to 100% mobile phase B for 5 min.

CNBr, Endoproteinase LysC and Chymotrypsin Digestions:

Mature human myostatin was digested with CNBr, which chemically cleaves peptide bonds after Met; with endoproteinase LysC, which cleaves peptide bonds after lysine; or with chymotrypsin, which cleaves after Phe, Tyr, Trp, Leu, and His. For chemical cleavage, about 20-35 micrograms of human myostatin (0.5 mg/ml) was incubated in 70% formic acid containing about 0.5 mg CNBr for 16 h at room temperature in the dark. For protease digestion, about 20-35 micrograms of human myostatin at 0.5 mg/ml was incubated in 10 mM ammonium acetate (pH 6.5) for 20 hrs at 37° C. with either LysC or chymotrypsin using myostatin-to-protease ratio of 20:1 (weight-to-weight basis). Samples from CNBr cleavage and proteolytic digestion experiments in 1-3 micrograms quantity were subjected to LC-MS/MS peptide mapping analysis. Similar peptide mapping analyses off-line from ESI-MS detection were also performed to collect individual peptide fractions for MALDI-MS analysis and binding assay.

In anti-myostatin antibody protection experiments, myostatin (20 micrograms; 0.5 mg/ml) was pre-incubated with antibody in two different quantities (30 and 120 micrograms; approximate myostatin dimer/Ab molar ratio=4:1 and 1:1, respectively) in 0.1M ammonium acetate, pH 6.5 for 1 h at room temperature. The samples were then digested with LysC and chymotrypsin as described above. Antibody alone in identical concentration was also digested and used as control as small amount of antibody may also be digested.

TCEP [tris(2-carboxyethyl)-phosphine]Reduction:

Disulfide bonds of native myostatin and HPLC-isolated cystine knot peptides from CNBr cleavage and LysC digestion samples were completely reduced by 100 mM TCEP in 0.05% trifluoroacetic acid for 4 hrs at 37° C. TCEP-reduced samples were then analyzed by LC-MS/MS analysis using conditions identical to LC-MS/MS peptide mapping. Reduced peptides were collected from peptide mapping analysis off-line from ESI-MS detection.

CNBr Cleavage:

HPLC chromatography of CNBr cleavage of human myostatin generated two main peaks with retention time of 58 and 80 min, respectively. The identity of the peptides in the HPLC peaks was determined with sample identification designated as peptides B and C (Table 6). Peptide B is a small fragment generated from cleavage of Met84 and Met101. Peptide C eluted approximately 5 min earlier than peptide A, the uncleaved myostatin recovered from HPLC analysis of native myostatin. By N-terminal sequencing, MALDI-MS and LC-MS/MS analysis, peptide C was identified as a cystine knot fragment containing sequence from 1-80 (molecular weight 9022 daltons) and 102-109 (molecular weight 836 daltons). The determined molecular weight of peptide C is approximately 19.7 kD, indicating that it is in dimeric form. After TCEP reduction of the CNBr cleavage sample followed by HPLC peptide mapping, peptides D and E as indicated in Table 6 were collected. Peptide D eluted at 58 min retention time was identified to have the same sequence as peptide B; and peptide E eluted at 80 min was identified to contain the 1-80 sequence, indicating disulfide bonds linked to peptide at sequence position 102-109 as well as the intermolecular disulfide bond had been completely reduced.

Figure 4:
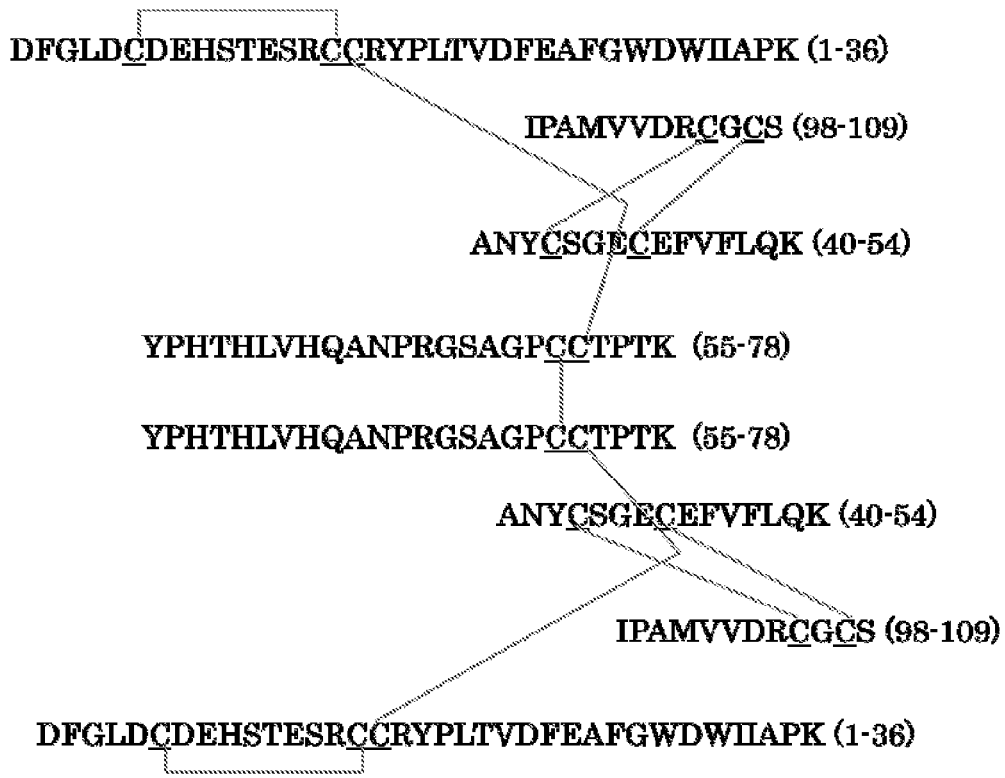
FIG. 4 illustrates Peptide G primary structure showing disulfide bonds linked four LysC peptides together to form cystine knot and another disulfide bond linked two 55-78 sequences together at Cys73. Peptide G exhibits binding to the antibody. The sequences disclosed in FIG. 4 are residues of SEQ ID NO: 25 corresponding to the positions as indicated.

LysC Digestion:

HPLC chromatography of the LysC digests only yielded four peaks. Peptide peaks at 8 and 38 min retention time were identified to be the peptides with sequence assigned at position 37-39, and 91-97, respectively. These two peptide peaks were not collected for binding assay. Peptide F collected at 61 min had a sequence assigned at 79-90 (Table 2). As confirmed by N-terminal sequencing and MALDI-MS, peptide G collected at 76 min contained four sequences linked by disulfide bonds and assigned at sequence position 1-36, 40-54, 55-78 and 98-109, indicating that the cystine knot structure is intact. This peptide peak was determined to have a molecular weight of 19.5 kD, confirming the existence of a dimeric form. Primary structure of peptide G with disulfide linkages among the four peptides is shown in FIG. 4.

After TCEP reduction of the LysC digest followed by LC-MS/MS peptide mapping, six peptides were then collected and further analyzed (Table 6). Peptide H at 38 min, a non-cysteine-containing peptide as described above, contains sequence 91-97. Peptides I, J, K, and M, collected from retention times at 43, 49, 60, and 79 min, were assigned to the following sequence positions, 55-78, 98-109, 40-54, and 1-36, respectively. These peptides are clearly derived from TCEP reduction of peptide G. Peptide L at 73 min contained mixed sequences with no sequence assignment.

In antibody protection experiments (in which myostatin pre-incubated with the antibody at two different antibody concentrations was proteolyzed with LysC), the peptide maps obtained from these experiments were identical to those obtained from digestion of myostatin alone. The structure of major peak at 78 min is completely identical to peptide G, the LysC cystine-knot peptide as described. The data indicated that 12A5-5 had no protection effect on myostatin proteolysis, i.e., the antibody does not provide proteolytic protection during LysC digestion.

Figure 5:
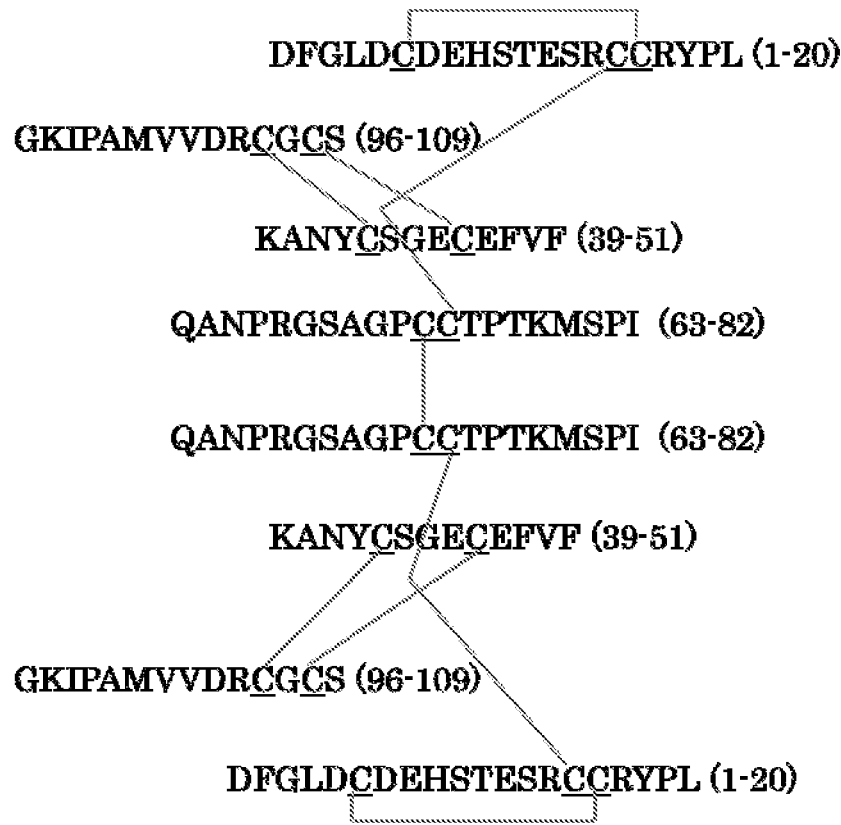
FIG. 5 presents Peptide N primary structure showing disulfide bonds linking four chymotryptic peptides together to form a cystine knot and a disulfide bond linking two 63-82 sequences together at Cys73. Peptide N does not bind the antibody. The sequences disclosed in FIG. 5 are residues of SEQ ID NO: 25 corresponding to the positions as indicated.

Chymotrypsin Digestion:

HPLC chromatography of the chymotryptic digests yielded multiple peaks. Sequence analysis was conducted on the peptide peaks recovered from HPLC. On-line ESI LC-MS analysis of the peptide digest was also performed to determine the precise mass of the peptides that were separated by HPLC. Chymotryptic cleavage generates a number of peptide peaks containing short di- to hepta-peptides detected at retention time 27.1 min (sequence position 53-57 and 53-59), 29 min (sequence position 30-31), 32.3 min (sequence position 52-57), 41 min (sequence position 53-60), 44 min (sequence position 52-60), 50 min (sequence position 87-95), 53 min (sequence position 30-38), 57 min (sequence position 28-31) and 58 min (sequence position 21-27). A large molecular weight and broad peptide peak around 67-73 min (designated as peptide N) was identified to contain the cystine knot structure, which is composed of four peptides (sequence positions 1-20, 25-38, 39-82, and 96-109) as confirmed by N-terminal sequencing. MALDI-MS analysis indicated peptide N had a molecular weight of 14.4 kD confirming the presence of a dimer while the MALDI-in-source partial fragmentation of disulfide bonds confirmed the peptide peak contains four peptides with the expected molecular weight corresponding to the sequence positions as shown in FIG. 5.

In the antibody protection experiment (in which myostatin pre-incubated with the 12A5-5 was proteolyzed with chymoytrypsin and analyzed by LC-MS/MS peptide mapping), at low antibody molar ratio, peptide peaks corresponding to peptides at sequence positions 30-31 and 28-31 and 32-38 exhibit decrease in their respective UV absorbance detection signals during peptide mapping, indicating that peptide(s) having the sequence between positions 28 and 38, was readily protected by the antibody from chymotrypsin digestion. At high antibody-to-myostatin molar ratio (close to 1:1), a large portion of proteolytic sites were protected. Significant decrease of peptide peaks were observed for peptides at sequence positions 21-27, 30-31, 28-31, 32-38, and 52-60, and a slight decrease for peptide 87-95. As a result a new peak (peptide P in Table 6) at 75 min with high UV absorbance was observed. These data indicate that the two regions in myostatin, located at sequence near position 21 to 31 and position 50 to 60, are in close interaction with the antibody so as to prevent chymotrypsin cleavage of peptide bonds at the above-mentioned peptides and thus necessary for the binding of 12A5-5 to myostatin.

TABLE 6

Myostatin peptides isolated from HPLC peptide mapping analysis of digests from CNBr, endoproteinase LysC and chymotrypsin digestions

| Peptide ID | Peptide name | Ret. Time (min) | Sequences |
| --- | --- | --- | --- |
| A | Native myostatin | 85 | 1-109 (dimer) |
| B | CNBr peptide | 58 | 85-101 |
| C | CNBr peptide (Cys knot) | 80 | 1-80 & 102-109 (dimer) |
| D | Reduced CNBr peptide | 58 | 85-101 |
| E | Reduced CNBr peptide | 80 | 1-80 |
| F | LysC peptide | 61 | 79-90 |
| G | LysC peptide (Cys knot) | 76 | 1-36, 40-54, 55-78 & 98-109 (dimer) |
| H | Reduced LysC peptide | 38 | 91-97 |
| I | Reduced LysC peptide | 43 | 55-78 |
| J | Reduced LysC peptide | 49 | 98-109 |
| K | Reduced LysC peptide | 60 | 40-54 |
| L | Reduced LysC peptide | 73 | mixed sequences |
| M | Reduced LysC peptide | 79 | 1-36 |
| N | Chymotryptic peptide (Cys knot) | 67-77 | 1-20, 39-51, 63-82 & 96-109 (dimer) |
| O | Reduced myostatin | 83 | 1-109 (monomer) |
| P | Chymotryptic peptide (Ab protected Cys knot) | 75 | 1-20, 21-82 & 96-109 (dimer) |

BIAcore® Binding Assay:

The strategy for characterizing the epitopes bound by anti-myostatin neutralizing monoclonal antibodies was to use various CNBr—, LysC— and chymotrypsin-generated human myostatin peptides and determine which peptides could be bound by the antibody. In one aspect, this was tested in a BIAcore® competition binding assay where the binding of 12A5-5 to human myostatin immobilized on a BIAcore® chip was determined in the presence or absence of each of the various isolated HPLC peptide fractions. In the absence of any competing peptides, 12A5-5 was able to bind the human myostatin on the chip and produce an RU (resonance unit) response. Pre-incubation of 12A5-5 with intact human myostatin in solution, followed by testing of binding to the chip demonstrated that the binding of the antibody to human myostatin in solution prevented the binding of the antibody to the human myostatin on the chip, thus validating the general principle of the competition assay. This general procedure was repeated individually for each peptide. A robust RU response was taken to indicate that the particular peptide being tested could not bind 12A5-5 in solution (hence 12A5-5 was free to bind the human myostatin that had been immobilized on the chip). Conversely, the absence of a robust RU response indicated that 12A5-5 was able to bind the myostatin peptide in solution (and was thus not able to bind to the immobilized myostatin). These binding patterns, coupled with the known identity of the various myostatin peptides were used to determine which regions of myostatin were important (or necessary) for the binding of antibody 12A5-5.

Figure 6:
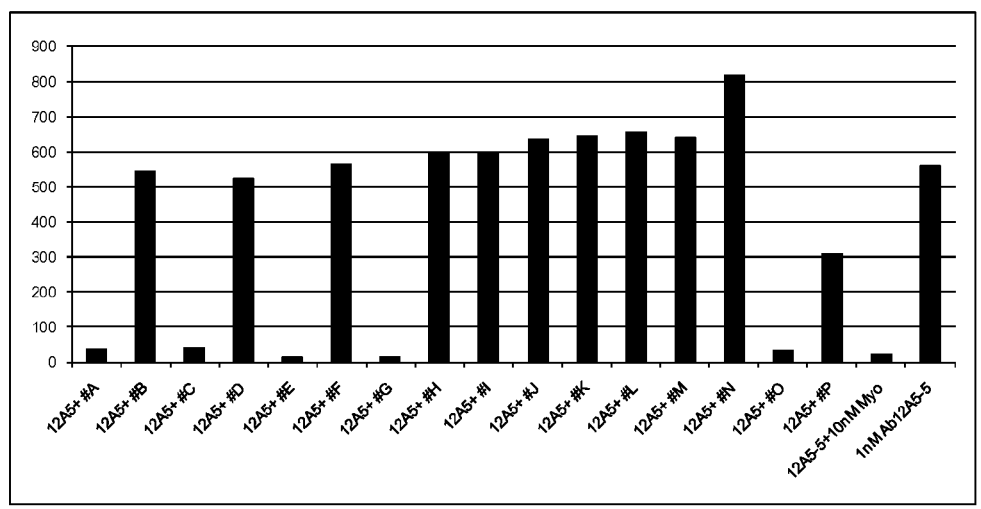
FIG. 6 represents results of the BIAcore® competition assay for non-reduced and TCEP-reduced peptide samples. Peptides A, C, E, G, O and P can all bind to antibody 12A5-5 thereby preventing 12A5-5 from binding to mature myostatin. None of other peptides tested, including the ones from TCEP reduction of peptide G and Peptide N, the cystine knot chymotryptic peptide, showed binding with the antibody.

FIG. 6 summarizes the binding assay for non-reduced and TCEP-reduced peptide samples. Peptide A (myostatin dimer recovered from HPLC), peptide C(CNBr peptide containing the cystine knot dimer), peptide E (reduced CNBr peptide, sequence position 1-80), peptide 0 (reduced intact myostatin monomer; sequence position 1-109), peptide G (LysC peptide containing the cystine knot dimer, sequence position 1-36, 40-54, 55-78 & 98-109), and peptide P (antibody-protected chymotryptic peptide containing the cystine knot dimer, sequence position 1-20, 21-82 & 96-109) can all bind to antibody based on BIAcore® competition assay. Peptide N (chymotryptic peptide containing the cystine knot dimer, sequence position 1-20, 39-51, 63-82 & 96-109) was not able to bind the antibody, nor were any of other peptides tested, including the ones obtained from TCEP reduction of peptide G. Moreover, the same was true for peptide M, which contains sequence identified in the antibody protection assay being involved in binding, indicating that the region between amino acids 21 and 31 is necessary for, but not sufficient for, binding of 12A5-5 to myostatin.

Figure 7:
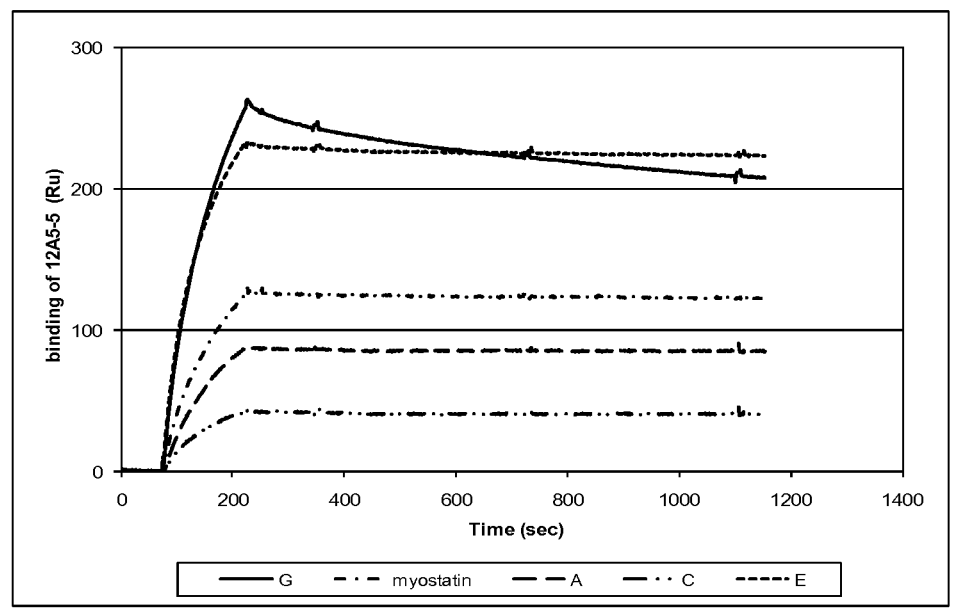
FIG. 7 illustrates results of the direct BIAcore® binding assay for Peptides A, C, E, and G, along with myostatin.
Figure 8:
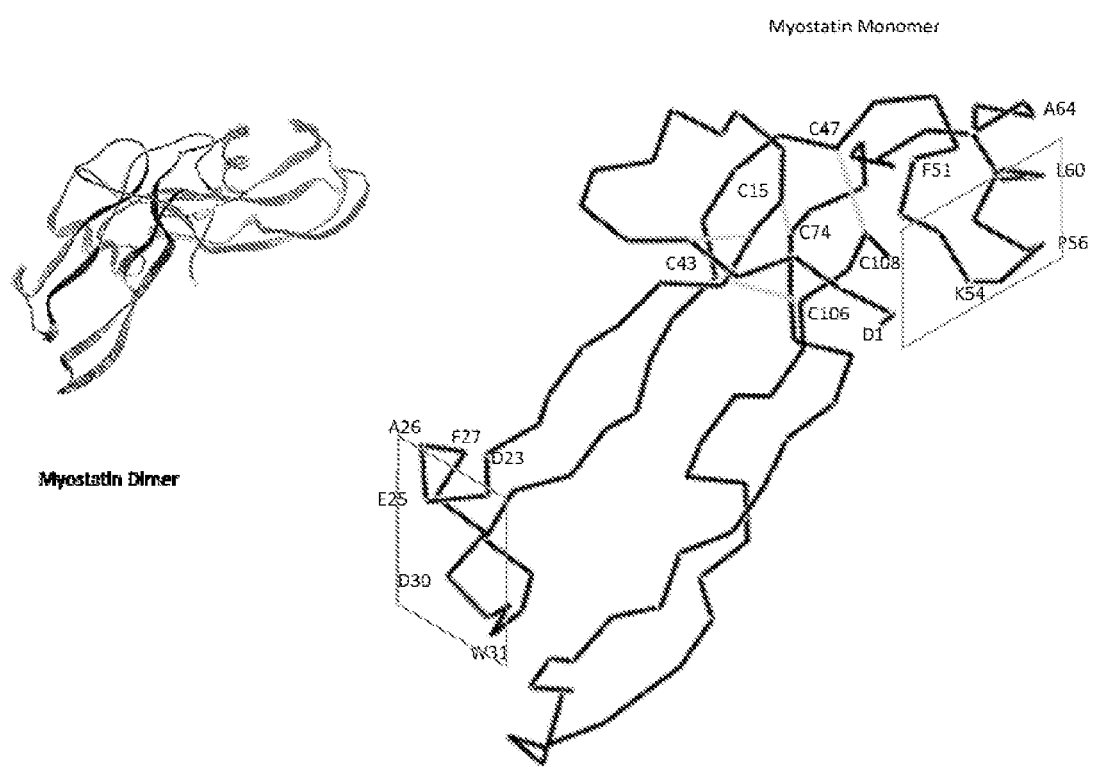
FIG. 8 represents the structures of myostatin dimer and monomer derived from the co-crystal structure of myostatin/follistatin complex (Cash et al., infra). The Cys residues involved in disulphide bonds are indicated, as are additional amino acid residues in the regions that are believed to be important for binding of 12A5-5 (indicated in the shaded rhomboids).

The ability of 12A5-5 to bind to peptides A, C, E, and G was further confirmed in a direct binding analysis, where the peptides were covalently immobilized to form peptide surfaces on BIAcore® chips. For this experiment, 25 nM of antibody was flown over the peptide surface at 80 microliter/min for 2.5 minutes, followed with flowing of buffer for 15 minutes. FIG. 7 shows the sensorgrams of the analysis. The association phase for antibody to bind with the immobilized peptides ended at ~200 s, which was the start point of dissociation phase of the antibody from the surfaces. The flat dissociation phase of peptides A, C, E and myostatin indicated stable complex formation between the antibody with these peptides, while the signal decrease in dissociation phase on peptide G surface indicated the complex formed between the antibody and peptide G is less stable. Comparing peptide G with peptide C, the decrease of antibody/peptide G complex stability appears to be largely due to the LysC cleavage at K54 in peptide G (FIG. 4), while there was no CNBr cleavage in the region around amino acids 50 to 60 in peptide C (which is missing a fragment between M78 and M101).

It is noteworthy that the sequence of myostatin right before K54 is EFVFLQ (SEQ ID NO: 54), while the corresponding sequence in GDF11 is EYMFMQ (SEQ ID NO: 55). In previous experiments, replacement of this region in myostatin with the corresponding region from GDF11 significantly decreased the interaction of the chimeric molecule with the antibody. The present data indicate that clipping around this region in myostatin also decrease its ability to form a complex with the 12A5-5 antibody, although it does not altogether abrogate it. Considering that binding affinity of 12A5-5 to myostatin is approximately 2 pM versus about 180 nM for GDF11, this region appears to be necessary for specific binding of the antibody to myostatin.

Taking the above data together, the regions in myostatin that are required for binding of myostatin to anti-myostatin neutralizing antibody 12A5 locate at sequence near position 21 to 31 and position 50 to 60 (depicted in FIG. 8). These two regions seem to be far in distance at primary sequence level. However, they are brought together at the three dimensional structure in dimeric form as demonstrated by the co-crystal structure of myostatin/follistatin complex (Cash et al., supra). FIG. 8 shows three dimensional myostatin dimer and monomer structures, in which each myostatin monomer forms a typical cystine knot structure. The two monomers are anti-parallel to each other and form myostatin dimer with a Cys73-Cys73 disulfide bond between two monomers. The anti-parallel structure of myostatin dimer makes the region around L52/L60 from one monomer in close proximity to region around F27/W31 in the other monomer. The data above suggest that antibody 12A5-5 requires both of the regions to achieve its strong binding activity.

We claim:

1. An isolated myostatin-specific antibody comprising at least one light chain and at least one heavy chain, wherein the light chain comprises a constant region and a variable region that comprises three complementarity determining regions (CDRs) and the heavy chain comprises a constant region and a variable region that comprises three CDRs, wherein the light chain CDRs are those disclosed in SEQ ID NO:39, SEQ ID NO:43, and SEQ ID NO:48, and the heavy chain CDRs are those disclosed in in SEQ ID NO:30, SEQ ID NO:33, and SEQ ID NO:36.

2. The antibody of claim 1, wherein the light chain variable region comprises the amino acid sequence set forth in SEQ ID NO:3, and the heavy chain variable region comprises the amino acid sequence set forth in SEQ ID NO:13 wherein residue 50 of SEQ ID NO:13 is the amino acid Glutamine.

3. The antibody of claim 1, wherein the light chain constant region is selected from the group consisting of a kappa and a lambda light chain, and the heavy chain constant region is selected from the group consisting of a mu, a delta, a gamma, an alpha, and an epsilon constant region.

4. The antibody of claim 3, wherein the antibody belongs to a subclass selected from the group consisting of IgG1, IgG2, IgG3 and IgG4.

5. A composition comprising the myostatin-specific antibody of claim 1 and a physiologically acceptable diluent, excipient or carrier.

6. An isolated nucleic acid encoding the myostatin-specific antibody according to claim 1.

7. A vector comprising the nucleic acid of claim 6.

8. An isolated host cell transfected or transformed with the vector of claim 7.

9. A method for the production of a myostatin-specific antibody comprising culturing the host cell of claim 8 under conditions promoting expression and recovering the myostatin-specific antibody from the culture medium.

10. A method of inhibiting at least one activity of myostatin, comprising administering a composition according to claim 5 to an individual such that at least one activity of myostatin is partially or fully inhibited.

* * * * *